(12) United States Patent
Lura et al.

(10) Patent No.: US 10,980,930 B2
(45) Date of Patent: Apr. 20, 2021

(54) FLUID CONNECTORS AND FLUID FLOW PATHS FOR AN INFUSATE CADDY

(71) Applicant: Medtronic, Inc., Minneapolis, MN (US)

(72) Inventors: David B. Lura, Maple Grove, MN (US); Christopher M. Hobot, Tonka Bay, MN (US); Martin T. Gerber, Maple Grove, MN (US); Thomas E. Meyer, Stillwater, MN (US)

(73) Assignee: Medtronic, Inc, Minneapolis, MN (US)

( * ) Notice: Subject to any disclaimer, the term of this patent is extended or adjusted under 35 U.S.C. 154(b) by 704 days.

(21) Appl. No.: 15/219,242

(22) Filed: Jul. 25, 2016

(65) Prior Publication Data

US 2017/0021076 A1 Jan. 26, 2017

Related U.S. Application Data

(60) Provisional application No. 62/196,907, filed on Jul. 24, 2015.

(51) Int. Cl.
*A61M 1/16* (2006.01)
*A61M 1/26* (2006.01)
(Continued)

(52) U.S. Cl.
CPC .......... *A61M 1/169* (2013.01); *A61M 1/1656* (2013.01); *A61M 1/1666* (2014.02);
(Continued)

(58) Field of Classification Search
None
See application file for complete search history.

(56) References Cited

U.S. PATENT DOCUMENTS

| 1,683,723 A | 9/1928 | William |
| 4,747,822 A | 5/1988 | Peabody |

(Continued)

FOREIGN PATENT DOCUMENTS

| CN | 202105667 | 1/2012 |
| DE | 202014104252 | 12/2015 |

(Continued)

OTHER PUBLICATIONS

International Search Report, Application PCT/US2016/043948, dated Feb. 2, 2017.

(Continued)

*Primary Examiner* — Jonathan M Peo
(74) *Attorney, Agent, or Firm* — Roger Hahn; Hahn & Associates

(57) ABSTRACT

The invention relates to fluid flow paths and fluid connectors for use with detachable containers that can be seated in an infusate caddy for use in a dialysis machine. The detachable containers can contain infusates or other solutes or materials such as disinfectants or cleaners, and can be conveniently seated in the infusate caddy. The detachable containers can be removed from the infusate caddy for restocking, cleaning, or resupply, as needed. The infusate caddy can be positioned or seated in a receiving compartment of a dialysis machine, and can also be removed, as needed. The fluid path and fluid connectors of the present invention provide the required fluid fittings, valve arrangements, pumps, and paddle assemblies for using the infusate caddy.

13 Claims, 18 Drawing Sheets

(51) Int. Cl.
*A61M 39/22* (2006.01)
*A61M 39/12* (2006.01)

(52) U.S. Cl.
CPC ............ *A61M 1/267* (2014.02); *A61M 39/12* (2013.01); *A61M 39/223* (2013.01); *A61M 2205/3337* (2013.01); *A61M 2209/08* (2013.01); *A61M 2209/082* (2013.01)

(56) References Cited

U.S. PATENT DOCUMENTS

| | | | |
|---|---|---|---|
| 4,950,230 | A | 8/1990 | Kendell |
| 5,032,265 | A | 7/1991 | Jha |
| 5,141,493 | A | 8/1992 | Jacobsen et al. |
| 5,643,201 | A | 7/1997 | Peabody |
| 5,744,031 | A | 4/1998 | Bene |
| 6,355,161 | B1 | 3/2002 | Shah |
| 6,645,191 | B1 * | 11/2003 | Knerr ................ A61J 1/2093 604/410 |
| 2002/0091371 | A1 | 7/2002 | Ritter |
| 2010/0051552 | A1 | 3/2010 | Rohde |
| 2010/0078092 | A1 | 4/2010 | Weilhoefer et al. |
| 2010/0312172 | A1 | 12/2010 | Hoffman |
| 2011/0017665 | A1 | 1/2011 | Updyke |
| 2011/0249916 | A1 | 10/2011 | Herrenbauer |
| 2012/0199205 | A1 | 8/2012 | Eyrard |
| 2013/0001165 | A1 | 1/2013 | Pohlmeier |
| 2013/0015302 | A1 | 1/2013 | Orter et al. |
| 2013/0062265 | A1 | 3/2013 | Balschat |
| 2014/0018727 | A1 | 1/2014 | Burbank |
| 2014/0217029 | A1 | 8/2014 | Meyer |
| 2017/0021076 | A1 | 1/2017 | Lura |
| 2017/0021079 | A1 | 1/2017 | Lura |
| 2017/0021086 | A1 | 1/2017 | Lura |

FOREIGN PATENT DOCUMENTS

| | | | |
|---|---|---|---|
| EP | 0714668 | | 6/1996 |
| EP | 2735322 | | 5/2014 |
| JP | 2006325668 | A | 12/2006 |
| WO | 9937342 | A1 | 7/1999 |
| WO | 0057935 | | 10/2000 |
| WO | WO-0057935 | A1 * | 10/2000 ........... A61L 2/0023 |
| WO | WO2000057935 | A1 | 10/2000 |
| WO | WO2009064984 | | 5/2009 |
| WO | 2011113572 | A1 | 9/2011 |
| WO | 2012138604 | A2 | 10/2012 |
| WO | WO2013077844 | | 5/2013 |
| WO | 2014121158 | A1 | 8/2014 |
| WO | 2015071247 | A1 | 5/2015 |
| WO | WO2017004449 | | 1/2017 |
| WO | WO2017/019640 | A1 | 2/2017 |

OTHER PUBLICATIONS

Written Opinion, Application PCT/2016/043948, dated Feb. 2, 2017.
International Search Report, Application PCT/US2016/043935, dated Feb. 2, 2017.
Written Opinion, Application PCT/US2016/043935, dated Feb. 2, 2017.
[NPL635] International Search Report, Application PCT/US2016/043948, dated Feb. 2, 2017.
[NPL636] Written Opinion, Application PCT/2016/043948, dated Feb. 2, 2017.
[NPL637] International Search Report, Application PCT/US2016/043935, dated Feb. 2, 2017.
[NPL638] Written Opinion, Application PCT/US2016/043935, dated Feb. 2, 2017.
PCTUS2017025876 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 Written Opinion dated Jun. 29, 2017.
PCT/US2017/025868 International Search Report dated Jun. 29, 2017.
Int'l Search Report PCT/US217/032337.
Internation Preliminary Report on Patentability, Application PCT/US2016/043948, dated Jul. 17, 2017.
Written Opinion, Application PCT/US2016/043935, dated Jun. 21, 2017.
International Preliminary Report on Patentability, Appliaction PCT/US2016/043950, dated Jul. 31, 2017.
International Preliminary Report on Patentability, Appliaction PCT/US2016/043935, dated Jul. 17, 2017.
European Office Action for App. No. 16757383.1, dated Mar. 13, 2020.
Chinese Office Action for App. No. 201680041324.7, dated Jun. 1, 2020.
Chinese Office Action for App. No. 201680041413.1, dated May 28, 2020.
European Search Report for App. No. 16760215.0, dated May 7, 2020.
European Search Report for App. No. 17724689.9, dated May 14, 2020.
European Office Action for App. No. 17724468.8, dated May 14, 2020.
Chinese Office Action for App. No. 201680041414.6, dated Jun. 9, 2020.
Chinese Office Action for App. No. 201680041414.6, dated Oct. 20, 2020.

* cited by examiner

FLUID CONNECTORS AND FLUID FLOW PATHS FOR AN INFUSATE CADDY

FIELD OF THE INVENTION

The invention relates to fluid flow paths and fluid connectors for use with detachable containers that can be seated in an infusate caddy for use in a dialysis machine. The detachable containers can contain infusates or other solutes or materials such as disinfectants or cleaners, and can be conveniently seated in the infusate caddy. The detachable containers can be removed from the infusate caddy for restocking, cleaning, or resupply, as needed. The infusate caddy can be positioned or seated in a receiving compartment of a dialysis machine, and can also be removed, as needed. The fluid path and fluid connectors of the present invention provide the required fluid fittings, valve arrangements, pumps, and paddle assemblies for using the infusate caddy.

BACKGROUND

Dialysis systems require specified amounts of solutions to be used during each dialysis session, such as sodium chloride, sodium bicarbonate and cation infusates. Further, many cations, such as potassium, calcium and magnesium, can cross the dialyzer and be removed from a patient during dialysis. These cations must be added back into the dialysate to maintain the concentration of these cations at a desired level. Sodium bicarbonate can be used during dialysis as a buffer to control the pH of the dialysate and to treat acidosis by delivering bicarbonate across the dialysis membrane to the patient receiving a treatment. The amounts of sodium chloride, sodium bicarbonate and other cations added to dialysate should be closely monitored and controlled. Further, the amounts of each of these solutions can vary considerably.

Systems and methods for ensuring appropriate fluid lines and fittings are used for adding and removing solutes to dialysate is required. In order to facilitate use of dialysis outside of a standard dialysis setting or by personnel having varying levels of skill, a method is needed that can ensure that each of the materials to be added to the dialysis system is connected to the correct pumps, valves, and connectors of the dialysis system. Further, there is a need for a system that can ensure that all necessary materials for dialysis are connected to the dialysis system and at the correct locations, allowing the proper amounts of each of the solutions to be added to the dialysate at the proper points in the dialysis system.

There is a further need for a method and system that can ensure proper fittings and connections of a dialysis system after a dialysis session is complete. There is a need for a system that can allow users of varying skill levels to easily configure the dialysis session including the necessary fittings and connections for disinfection, and ensure that the dialysis system can be used outside of a standard dialysis clinical setting, such as in a patient's home.

There is further a need for a system of fluid lines, pumps and valves that are configured so that they are attachable to an infusate caddy for use in dialysis. There is a need for the system to be configured to ensure that the proper containers connect to the proper fluid lines, valves and pumps.

SUMMARY OF THE INVENTION

The first aspect of the invention relates to a flow path for dialysis. In any embodiment, the flow path can include at least one fluid line on the flow path for dialysis, said fluid line fluidly connectable to at least one detachable container; a fluid pump positioned on the fluid line for removing or introducing a fluid to the detachable container; a fluid connector fluidly connectable to the detachable container wherein the at least one detachable container is selected from the group consisting of a sodium chloride infusate container, a sodium bicarbonate infusate container, and a cation infusate container.

In any embodiment, the flow path can include a paddle assembly having at least one independently movable paddle, wherein the fluid connector is positioned at a distal end of the paddle.

In any embodiment, the detachable container can have a fitting feature complementary to an infusate caddy.

In any embodiment, the flow path can have a first fluid line fluidly connectable to the sodium chloride infusate container; a second fluid line fluidly connectable to the sodium bicarbonate infusate container; wherein the first fluid line and the second fluid line are in fluid connection with a dialysate flow path.

In any embodiment, the first fluid line and second fluid lines can connect to a first valve that connects to a third fluid line; the third fluid line can connect to the dialysate flow path; and a fluid pump can control movement of fluid between the dialysate flow path and the sodium chloride infusate container and the sodium bicarbonate infusate container.

In any embodiment, a fourth fluid line can be fluidly connectable to the sodium chloride infusate container and a fifth fluid line fluidly connectable to the sodium infusate bicarbonate container; wherein the fourth fluid line and the fifth fluid line are fluidly connected to a second valve; wherein the second valve connects the fourth fluid line and fifth fluid line to a sixth fluid line; and wherein the sixth fluid line connects the second valve to the dialysate flow path.

In any embodiment, the fourth fluid line and the fifth fluid line can be connected into a single fluid line; wherein the single fluid line connects to the second valve; wherein the second valve connects the single fluid line and a sixth fluid line; and wherein the sixth fluid line connects the second valve to the dialysate flow path.

In any embodiment, the second valve can be a two way valve.

In any embodiment, the second valve can be a three-way valve.

In any embodiment, the fluid pump can be a bi-directional pump.

In any embodiment, the flow path can include at least one fluid line fluidly connectable to a disinfectant container in an infusate caddy.

In any embodiment, the third fluid line can be connected to a third valve; wherein the third valve connects to a seventh fluid line and an eighth fluid line; wherein the seventh fluid line connects to the dialysate flow path downstream of a sorbent cartridge and the eight fluid line connects to the dialysate flow path upstream of the sorbent cartridge.

Any of the features disclosed as being part of the first aspect of the invention can be included in the first aspect of the invention, either alone or in combination.

The second aspect of the invention is directed to a paddle assembly. In any embodiment, the paddle assembly can include at least one independently movable paddle, wherein a fluid connector is positioned at a distal end of the paddle; the paddle can have a fluid line disposed inside the paddle, wherein the fluid line is fluidly connectable to a fluid flow path in a dialysis machine; and a hollow hinge having a central flow line in communication with each one of the fluid lines in the independently movable paddles wherein a proximal base of each of the independently movable paddles is rotatable about the hollow hinge.

In any embodiment, the fluid connector can be fluidly connectable to a fluid connector on a detachable container.

In any embodiment, the paddles can be lockable paddles configured to lock the detachable container in place.

Any of the features disclosed as being part of the second aspect of the invention can be included in the second aspect of the invention, either alone or in combination.

The third aspect of the invention is drawn to a method. In any embodiment, the method can include selectively opening or closing one or more valves in a flow path; pumping fluid using one or more pumps from at least one detachable container through a fluid connector into a dialysate flow path through at least one fluid line; wherein the at least one detachable container is seated within an infusate caddy and contains at least one solute for use in dialysis.

In any embodiment, the method can include selectively opening or closing one or more valves to form a flow path fluidly connected to multiple detachable containers; and pumping fluid from the multiple detachable containers to the flow path using one or more pumps.

In any embodiment, the flow path can be the flow path of the first aspect of the invention.

In any embodiment, the infusate caddy can be seated inside a receiving compartment of a dialysis machine.

In any embodiment, the infusate caddy can have a fitting feature selected from any one of a specified geometry, size, or shape.

In any embodiment, any one of the specified geometry, size, or shape can be complementary to a corresponding geometry, a corresponding size, or a corresponding shape of the detachable container.

In any embodiment, the fitting feature can be a curved wedge protrusion disposed on an interior side of the infusate caddy.

In any embodiment, the method can include the step of pumping fluid from the dialysate flow path into the at least one detachable container through the fluid connector.

DETAILED DESCRIPTION OF THE INVENTION

Figure 1A:
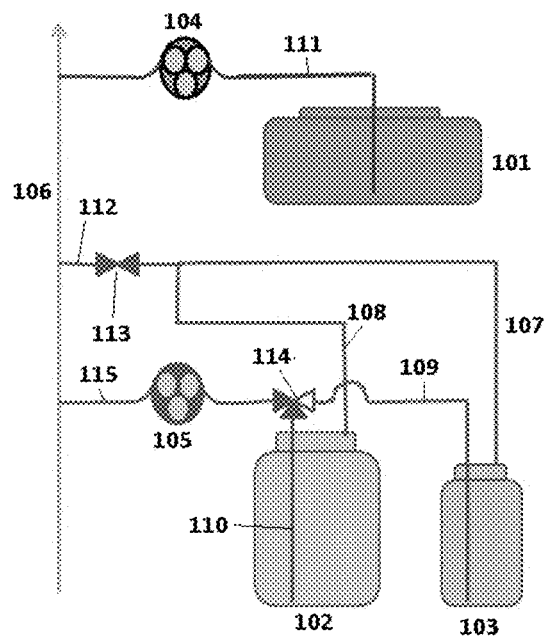
FIG. 1a shows a flow path of the connectors, pumps and valves in an infusate caddy using one two-way valve and one three-way valve.

Unless defined otherwise, all technical and scientific terms used herein generally have the same meaning as commonly understood by one of ordinary skill in the relevant art.

The articles "a" and "an" are used to refer to one or to over one (i.e., to at least one) of the grammatical object of the article. For example, "an element" means one element or over one element.

The term "aligned for connection" refers to a configuration of components wherein the components are situated so that a fluid connection can be formed between the components.

The terms "sodium bicarbonate infusate container," "sodium bicarbonate container," or "bicarbonate container" refer to a container that can be a stand-alone container or alternatively can be integrally formed with an apparatus for hemodialysis, hemodiafiltration, or hemofiltration. The bicarbonate container can store a source of buffering material, such as sodium bicarbonate, and can be configured to interface with at least one other functional module found in systems for hemodialysis, hemodiafiltration, or hemofiltration. The bicarbonate container can contain at least one fluid pathway and include components such as conduits, valves, filters or fluid connection ports. The bicarbonate container may be single use, or may be refilled and used multiple times, for example, by refilling the bicarbonate container to replace the bicarbonate material which can be a liquid or solid form.

The term "bi-directional pump" refers to a device configured to perform work on a fluid to cause the fluid to flow alternatively in either of two opposing directions.

The term "cation infusate container" refers to a source from which cations can be obtained. Examples of cations include, but are not limited to, calcium, magnesium and potassium. The source can be a solution containing cations or dry compositions that are hydrated by the system. The cation infusate container is not limited to cations and may optionally include other substances to be infused into a dialysate or replacement fluid; non-limiting examples can include glucose, dextrose, acetic acid and citric acid.

A "central flow line" is a fluid line through the middle of a component.

A "citric acid solution" is a solution containing citric acid, $C_6H_8O_7$, dissolved in water.

The term "complementary," as used to describe fitting features, refers to one or more fitting features on a first component that are designed to pair or mate with one or more fitting features on a second component. For example, a first component may have a receiving compartment of particular dimensions, and the second component may be the same dimensions, such that the second component can mate within the receiving compartment.

The term "comprising" includes, but is not limited to, whatever follows the word "comprising." Use of the term indicates the listed elements are required or mandatory but that other elements are optional and may be present.

The term "configured to lock" means any particular form, alignment, shape, design, marking, or arrangement suitable for allowing one component to keep two components or containers from inadvertent detachment.

"Connectable" refers to two components that can be attached. In any embodiment, connectable components can be fluidly connectable.

A "connector" and "for connection" describe the concept of forming a fluid connection between two components wherein fluid or gas can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "corresponding geometry," "corresponding size," or "corresponding shape" refer to the geometry, size, or shape of a container or fitting feature complementary to a fitting feature on a second container or compartment.

A "curved wedge protrusion" is a fitting feature extending inwardly towards the center of the compartment. A curved wedge protrusion in one, non-limiting embodiment can be disposed on an interior side of a receiving compartment.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional time or effort. The detached component can be optionally reattached to the system, module, cartridge or other component. A detachable module can often be part of a reusable module.

"Dialysis configuration" refers to a configuration of containers, connectors and fluid pathways that allows for use of the containers, connectors and fluid pathways in a dialysis session.

A "dialysate flow loop," or a "dialysate flow path," is a route in which a fluid can travel during dialysis.

"Dialysis" or "dialysis therapy" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis machine" is a system comprising a dialyzer, pumps, valves and fluid lines that is used to carry out a dialysis session.

A "dialysis machine connector" is a connector for connecting a dialysis machine to an external component.

A "dialysis system" is a collection of components necessary to carry out dialysis.

"Disinfection configuration" refers to a configuration of containers, connectors and fluid pathways that allows for use of the containers, connectors and fluid pathways in order to disinfect a system.

A "disinfection container" is a source from which a disinfection solution, such as citric acid, can be obtained. The source can be a solution containing disinfecting chemicals or dry compositions that are hydrated by the system.

A "disinfection solution," or a "disinfectant" is a solution that can disinfect any component, connector or container of a dialysis system.

The term "distal end" refers to the side of a component situated furthest away from the point of attachment of the component.

A "fitting feature" is any protrusion, indentation, groove, ridge, having any shape, size, or geometry that serves to ensure that only a corresponding fitting feature complementary to the fitting feature is capable of forming a connection or fit to the corresponding fitting feature. The fitting feature also includes non-mechanical means for ensuring complementary connection such as magnets placed at particular locations, or visual or aural indicators such as color, lettering, or sound. The fitting feature can be affixed, integral, or labeled on a component or surface to ensure that a corresponding feature on a desired component or surface can mate or connect to the component or surface having the fitting feature.

A "fluid" is a liquid substance optionally having a combination of gas and liquid phases in the fluid. Notably, a liquid can therefore also have a mixture of gas and liquid phases of matter.

The term "fluid connection," "fluidly connectable," or "fluidly connected" refers to the ability to pass fluid, gas, or mixtures thereof from one point to another point. The two points can be within or between any one or more of compartments, modules, systems, and components, all of any type.

A "fluid line" is any conduit through which a fluid can move.

The term "fluid pump," or "pump" refers to any device that causes the movement of fluids or gases by applying suction or pressure.

"Geometry" refers to the size or shape of a component.

The term "hollow hinge" refers to a component about which a connected component can rotate, the hollow hinge having an interior opening allowing fluid or gas to move through the hollow hinge.

The terms "independently moveable" or to "move independently" refer to the ability to move one component without moving a second component. The first component can move independently of the second component.

The term "infusate caddy," "infusate caddy," or "caddy" refers to a container detachably removable from a dialysis system, the caddy configured to hold one or more other containers. In any embodiment the caddy can include one or more connectors for fluid connection from the containers to the dialysis system.

An "infusate container" is a container adapted to contain one or more fluids for use in dialysis. The infusate container can at times hold dry chemicals that are later able to be reconstituted with a fluid to form a further useable fluid within the system.

The term "interior side" refers to an interior boundary of a component.

The terms "introducing fluid" or to "introduce fluid" mean to add fluid into a component, compartment, or portion of a system.

To "lock" means to connect two components such that the components will resist inadvertent detachment.

The term "lockable paddles" refers to paddles having a means for securing the paddle to another component, such that the paddle and the other component will resist inadvertent detachment. In any embodiment, lockable paddles can also comprise fluid connectors for fluid connection from one component to another.

A "moveable paddle" is a paddle that can be moved into a different alignment or configuration, such as by rotation.

"Moving fluid bi-directionally" or to "move fluid bi-directionally" refers to the ability of a system to cause fluid to move through a fluid line in either direction. The movement of fluid bi-directionally can be accomplished by a single pump capable of moving fluid in two directions, or by multiple pumps capable of moving fluid in opposite directions.

The term "paddles" refers to components that can be rotatable, and in a preferred embodiment the paddles rotationally extend axially from a central axis. Multiple paddles can be used together as a "paddle assembly."

The terms "pathway," "conveyance pathway," "fluid flow path," and "flow path" refer to the route through which a fluid or gas, or both, such as dialysate or blood, travels.

The term "positioned" refers to the location of a component.

The term "positioned to control" refers to a placement of pumps, valves, or other components that allows the components to direct the movement of fluid into and out of a fluid flow path or containers.

The term "priming configuration" refers to a configuration of containers, connectors and fluid pathways that allows for priming of the containers, connectors and fluid pathways.

The terms "pumping," "pumped," or to "pump" refers to moving or flowing a fluid using a pump of any type known to those of ordinary skill in the art.

The term "removable" or "removed" relates to any component of the present invention that can be separated from a system, module, cartridge or any component of the invention.

The term "removing fluid" or to "remove fluid" means to move fluid out of a component, compartment, or portion of a system.

To "rotate about" or "rotatable about" refer to the movement of a component in a circular direction around an axis.

The term "seated" refers to a component positioned on or in a second component.

"Shape" refers to the three dimensional form of a component.

"Size" refers to the area, surface area, or volume of a container or component.

The terms "sodium bicarbonate reservoir" and "sodium bicarbonate container" refer to an object that can be a stand-alone enclosure or alternatively can be integrally formed with an apparatus for hemodialysis, hemodiafiltration, or hemofiltration. The object can store a source of sodium bicarbonate in solid and/or solution form, and can be configured to interface with at least one other functional module found in systems for hemodialysis, hemodiafiltration, or hemofiltration. The sodium bicarbonate reservoir or container can contain at least one fluid pathway and include components such as conduits, valves, filters or fluid connection ports.

The terms "sodium chloride infusate container" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. The sodium chloride reservoir or container can contain at least one fluid pathway and include components such as conduits, valves, filters or fluid connection ports.

A "solute" is a substance dissolved in, or intended to be dissolved in, a solvent.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

Infusate Caddy Configuration

Figure 1B:
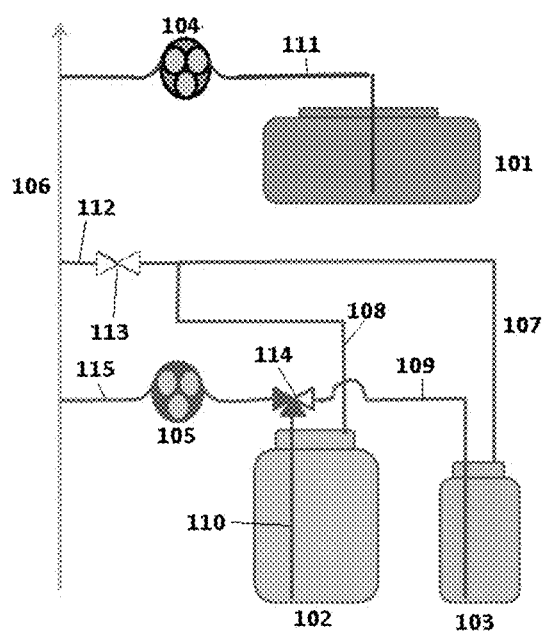
FIG. 1b shows a dialysate flow path of the connectors, pumps and valves in an infusate caddy configured for flushing and filling the dialysis system.

The first and second aspects of the invention relate to the fittings, connectors, pumps and valves for an infusate caddy. The infusate caddy can include a sodium chloride container, a sodium bicarbonate container and a cation infusate container. FIGS. 1a and 1b show a possible configuration for an infusate caddy, allowing sodium chloride, sodium bicarbonate, and cation infusates to be used in setting up and performing dialysis. Sodium chloride container 103 can be fluidly connected to a first fluid line 107, which can allow fluid or gas to move between dialysate flow loop line 106 and sodium chloride container 103. Sodium chloride container 103 can also be fluidly connected to a fourth fluid line 109, allowing fluid from the sodium chloride container 103 into the rest of the dialysate flow path 106 through valve 114 and pump 105. Sodium bicarbonate container 102 can be fluidly connected to a second fluid line 108, allowing fluid and gas to move between the sodium bicarbonate container 102 and dialysate flow loop line 106. Sodium bicarbonate container 102 can also be fluidly connected to a fifth fluid line 110, allowing fluid or gas to move from between sodium bicarbonate container 102 and dialysate flow loop line 106 through valve 114 and pump 105. First valve 113, which can be a two-way valve, is positioned to control the movement of fluid or gas between dialysate flow loop line 106 and the sodium chloride container 103 and sodium bicarbonate container 102 through sixth fluid line 112. Second valve 114, which can be a three-way valve, is positioned to control the movement of fluid and gas between either sodium chloride container 103 or sodium bicarbonate container 102 and the dialysate flow loop line 106 via seventh fluid line 115. Pump 105 can provide the driving force necessary to introduce or remove fluid to or from the sodium chloride container 103 or sodium bicarbonate container 102 to dialysate flow loop line 106. Pump 105 can be a positive displacement pump, such as a peristaltic pump that occludes seventh fluid line 115 and prevents liquid from flowing uncontrolled from dialysate line 106 into sodium bicarbonate container 102 or sodium chloride container 103. Pump 105 can be a bi-directional pump, capable of pumping fluids and gas in either direction through seventh fluid line 115. Alternatively, multiple pumps can be utilized that can move fluid in opposite directions as opposed to a single pump capable of moving fluid in two different directions. Cation infusate container 101 can be fluidly connected to third fluid line 111. Cation infusate pump 104 is positioned to introduce fluid to or remove fluid from cation infusate container 101, through the third fluid line 111, into the dialysate flow loop line 106. Cation infusate pump 104 can be a positive displacement pump, such as a peristaltic pump that occludes third fluid line 111 and prevents liquid from flowing uncontrolled from dialysate line 106 into cation infusate container 101.

In FIG. 1, the valves 113 and 114 are shown as open to flow lines where the valve portion is filled, and closed to flow lines where the valve portion is unfilled. First valve 113 is shown open to the dialysate flow loop line 106 and second valve 114 is shown in a state that directs flow to occur only between pump 105 and sodium bicarbonate container 102 and prevents flow between pump 105 and sodium chloride container 103. Because first valve 113 is open, fluids and gas can pass between dialysate flow loop line 106 and either the sodium bicarbonate container 102 or sodium chloride container 103.

As shown in FIG. 1b, after the caddy is attached to the dialysis system, the system must be flushed of any fluid, filled with water, and then primed. The valve configuration in FIG. 1b can be used during flushing and filling the dialysis system. If pump 105 occludes seventh fluid line 115 and by keeping first valve 113 closed to the dialysate flow loop line 106 during flushing and filling, no citric acid or other disinfectants can enter the sodium chloride container 103 or sodium bicarbonate container 104.

Figure 2:
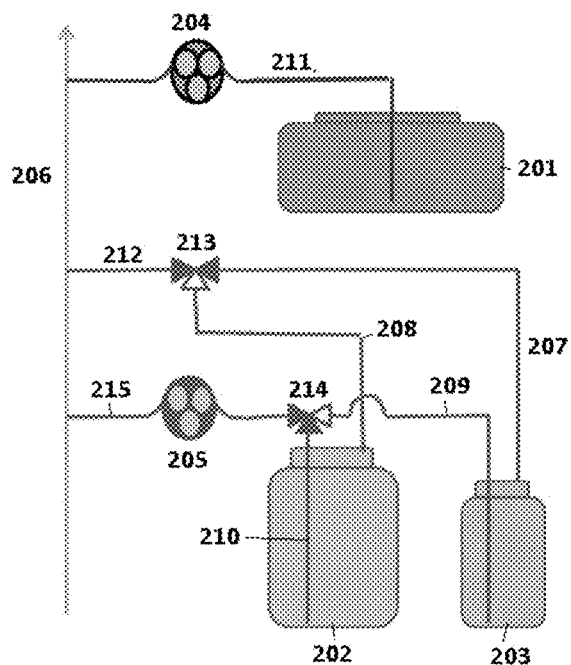
FIG. 2 shows a flow path of the connectors, pumps and valves in an infusate caddy using two three-way valves.

FIG. 2 shows a configuration of caddy connectors, containers, valves and pumps using two three-way valves positioned to control the movement of fluids. In FIG. 2, line 206 can represent the main operational dialysate flow loop, or line 206 can represent a fluid connector between the caddy and the rest of the dialysis system. Cation infusate container 201, sodium bicarbonate container 202 and sodium chloride container 203 can be placed in a caddy.

Sodium chloride container 203 can be fluidly connected to a first fluid line 207, which allows fluid or gas to enter the sodium chloride container 203. The sodium chloride container 203 can also be fluidly connected to a fourth fluid line 209, which allows fluid or gas to leave the sodium chloride container 203 and enter the rest of the dialysis system through line 206. Sodium bicarbonate container 202 can be connected to a second fluid line 208, which allows fluid or gas to enter the sodium bicarbonate container 202, and also can be fluidly connected to a fifth fluid line 210, which allows fluid or gas to leave the sodium bicarbonate container 202 and enter the dialysate flow loop through line 206. The movement of fluid or gas from dialysate flow loop 206 into the sodium chloride container 203 or sodium bicarbonate container 202 can be controlled by a first valve 213. Valve 213 is positioned to control the movement of fluid or gas from sixth fluid line 212, fluidly connected to line 206, into first fluid line 207 and second fluid line 208, controlling the movement of fluid or gas into the containers. The introduction or removal of fluid from the sodium chloride container 203 or sodium bicarbonate container 202 can be controlled by second valve 214. Valve 214 can allow or prevent fluid from moving from fourth fluid line 210 and fifth fluid line 209 into seventh fluid line 215, which connects to line 206. Bicarbonate pump 205 can draw fluid from the sodium chloride container 203 or sodium bicarbonate container 202 into line 206, and to the rest of the dialysis system. Bicarbonate pump 205 can be a bi-directional pump, capable of moving fluid from seventh fluid line 215 into line 206, or from line 206 into seventh fluid line 215. The cation infusate container 201 can be fluidly connected to a third fluid line 211, which allows fluid to move between the cation infusate container 201 and the dialysate flow loop 206. Adding fluid from the cation infusate container 201 to the dialysate flow loop 206 can be controlled by cation infusate pump 204. The valves and pumps shown in FIG. 2 can be located inside of the caddy, or with the rest of the dialysis system outside of the caddy.

Figure 3:
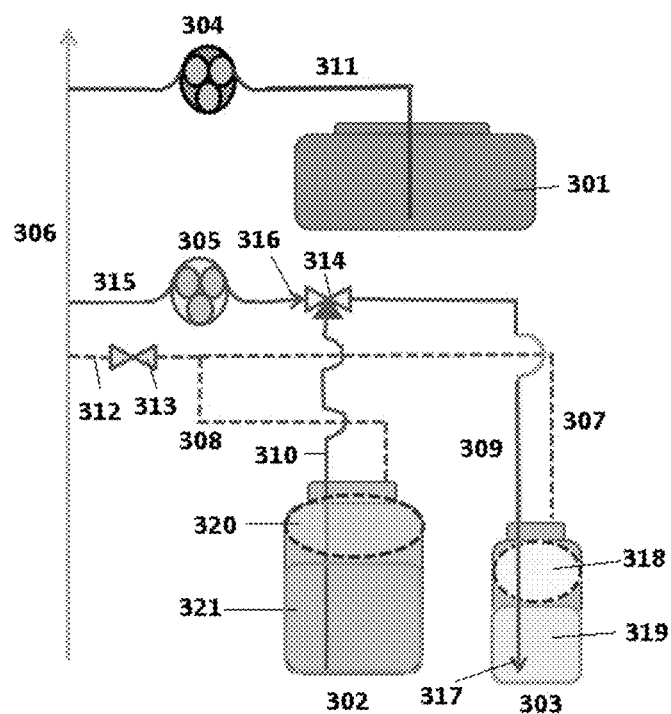
FIG. 3 shows a flow path of the connectors, pumps and valves in an infusate caddy using one two-way valve and one three-way valve controlling fluid to a sodium chloride and a sodium bicarbonate container.

FIGS. 3-6 show flow paths for caddy containers, connectors, valves and pumps using a two-way valve and a three-way valve and using the valves, pumps and containers to prepare a dialysis system for use. In FIG. 3, the flow path can contain a cation infusate container 301, a sodium bicarbonate container 303, and a sodium chloride container 304. Any one or more containers can initially contain a solid source, which can be dissolved to create a solution for dialysis. For example, the sodium chloride container 303 can contain either sodium chloride solids or sodium chloride concentrate in the bottom section 319 of the sodium chloride container 303. The top section 318 of sodium chloride container 303 can contain air. The bottom section 321 of sodium bicarbonate container 302 can initially contain sodium bicarbonate solids or a sodium bicarbonate concentrate. The top section 320 of sodium bicarbonate container 302 can initially contain air.

Sodium chloride container 303 can be connected to first fluid line 307 and fourth fluid line 309. Fluid line 307 can connect the sodium chloride container 303 to valve 313. First valve 313 can also connect to sixth fluid line 312, which in turn connects to the main dialysate flow loop 306. Fourth fluid line 309 can connect to second valve 314, which also connects to seventh fluid line 315 and the main dialysate flow loop 306. Pump 305 is positioned to introduce or remove fluid through lines 315 and 309.

Sodium bicarbonate container 302 can be connected to second fluid line 310 and fifth fluid line 308. Fifth fluid line 308 can also connect to first valve 313. Sixth fluid line 310 can also connect to second valve 314. Cation infusate container 301 can be connected by third fluid line 311 to the main dialysate flow loop 306. Pump 304 can control the movement of fluid through line 311.

Either or both of pumps 304 and 305 can be capable of moving fluid bi-directionally. That is, either one or both of the pumps can move fluid from the containers within the infusate caddy to the main dialysate flow loop 306, or from the main dialysate flow loop 306 to any of the containers within the infusate caddy.

In FIG. 3, the valves and pumps are configured for priming the sodium chloride container 303. The dotted lines denote fluid lines containing gas, while solid lines denote fluid lines containing liquid. The light colored portions of a valve denote the valve is open in those directions, while the dark colored portions denote the valve is closed in those directions. To prime the sodium chloride container 303, pump 305 can pump water from the main dialysate flow loop 306 into seventh fluid line 315, as shown by arrow 316. Second valve 314 can be used to direct the water through fourth fluid line 309 and into sodium chloride container 303, as shown by arrow 317. The water can dissolve the sodium chloride solids in the bottom section 319 of sodium chloride container 303 to create a sodium chloride solution that is approximately saturated. As water enters sodium chloride container 303 through fourth fluid line 309, air can be displaced to the dialysis flow loop 306 through first fluid line 307 and removed by a degasser (not shown). Sodium chloride container 303 can be partially filled with water 319 and an amount of air 318 can remain in the top section 318 of sodium chloride container 303. Because sodium chloride container 303 is only partially filled with water 319 and an air volume 318 remains at the top of sodium chloride container 303, NaCl solution is prevented from flowing out of sodium chloride container 303, through first fluid line 307 to sodium bicarbonate container 302 and dialysate flow loop 306. The sodium chloride container 303 can initially be nearly completely filled with sodium chloride solids. The sodium chloride container 303 can be filled only partially with water. As sodium chloride concentrate is metered out of the sodium chloride container 303 during use, additional fluid can be introduced into the sodium chloride container 303, dissolving some of the remaining sodium chloride solids in the bottom section 319 of the container 303, so that the sodium chloride solution remains approximately saturated. One skilled in the art will understand that additional materials can be included in caddy containers not shown in FIG. 2. For example, urease may be included for addition to a sorbent cartridge. Further, additional infusates, such as barium carbonate, may be added to control solute concentrations in the dailysate. Any number of additional infusate containers can be primed in the same fashion as described for sodium bicarbonate container 302 or sodium chloride container 303.

Pump 304 can occlude third fluid line 311 and prevent flow in either direction between cation infusate container 304 and the main dialysis flow loop 306 and pump 305 can be capable of occluding seventh fluid line 315 and simultaneously prevent flow in either direction between the main dialysis flow path 306 and both the sodium bicarbonate container 302 and sodium chloride container 303. Non-limiting examples of such pumps include positive displacement pumps such as roller-type peristaltic pumps and reciprocating piston pumps.

Figure 4:
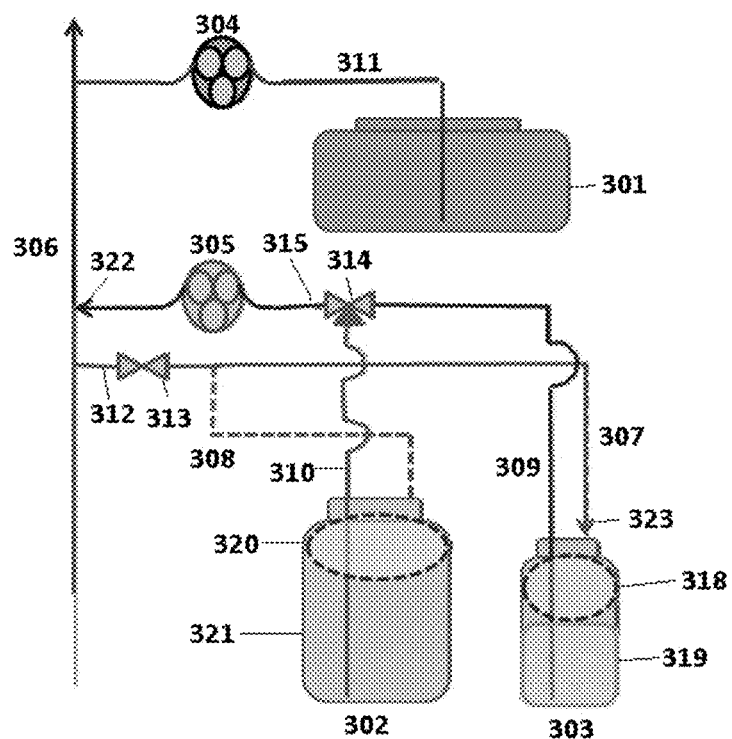
FIG. 4 shows a flow path of the connectors, pumps and valves in an infusate caddy using one two-way valve and one three-way valve controlling fluid to a sodium chloride and sodium bicarbonate container.

FIG. 4 shows the pumps, valves and connections as configured for metering sodium chloride from sodium chloride container 303 into dialysis flow path 306. The components in FIG. 4 can be the same as the components in FIG. 3; as such, the same reference numbers in each of the figures refer to the same components. Pump 305 can be reversed from the direction shown in FIG. 3, so that instead of pumping water from the dialysate flow loop 306 into the sodium chloride container 303, the pump 305 instead pumps the sodium chloride solution from the sodium chloride container 303 into the dialysis flow loop 306, as shown by arrow 322. Second valve 314 is operated to flow the sodium chloride solution to move from the sodium chloride container 303 into the dialysate flow loop 306 by action of pump 305, while preventing any movement of fluid out of the sodium bicarbonate container 302 through second fluid line 310. As fluid is moved out of the sodium chloride container 303, first valve 313 can be opened to allow fluid to move from the dialysate flow loop 306 into the sodium chloride container 303, as shown by arrow 323, thereby keeping a relatively constant amount of fluid in both the dialysate flow loop and the containers within the caddy. Concentration sensors, such as conductivity sensors, can be included to ensure that the fluid in the dialysate flow loop 306 has the desired sodium chloride concentration.

Figure 5:
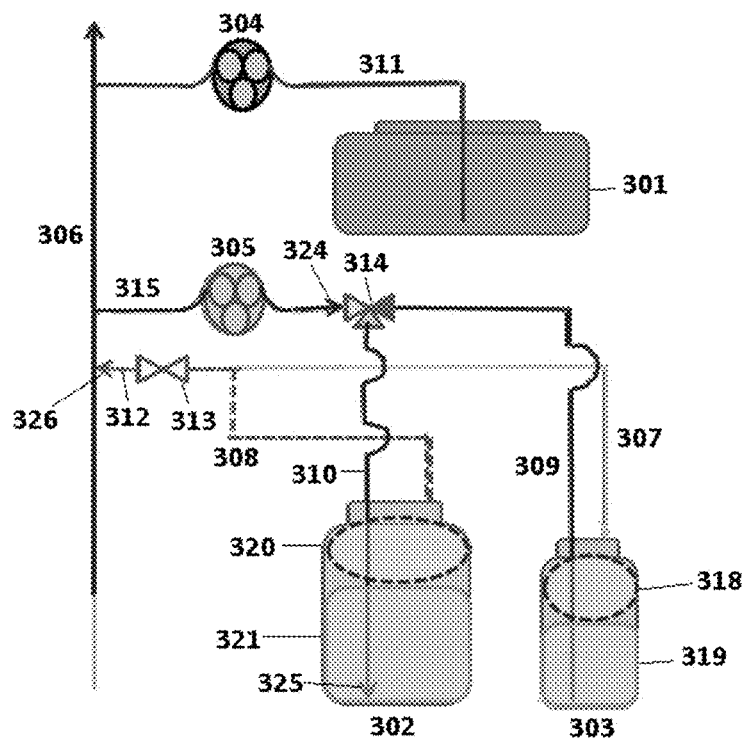
FIG. 5 shows a flow path of the connectors, pumps and valves in an infusate caddy using one two-way valve and one three-way valve controlling fluid to the sodium chloride and sodium bicarbonate containers.

FIG. 5 shows the same system configured for priming of the sodium bicarbonate container 302. Second valve 314 can be operated to allow water from the dialysate flow loop 306 into the sodium bicarbonate container 302 by action of pump 305 through second fluid line 310 as represented by arrows 324 and 325, while preventing water from entering the sodium chloride container through fourth fluid line 309. The sodium bicarbonate container 302 can contain sodium bicarbonate solids. The water added to the sodium bicarbonate container 302 can dissolve the sodium bicarbonate to make an approximately saturated sodium bicarbonate solution in the bottom section 321 of the sodium bicarbonate container 302. Sodium bicarbonate container 302 can be partially filled such that a volume of air 320 can remain in the top section 320 of the sodium bicarbonate container 302. The air remaining in the top section 320 can prevent sodium bicarbonate solution from flowing out of the sodium bicarbonate container 302 through fifth fluid line 308, to sodium chloride container 303 and the dialysate flow loop 306. As water is introduced to sodium bicarbonate container 302 through second fluid line 310, air can be displaced to the dialysis flow loop 306 through sixth fluid line 312 and first valve 313, as represented by arrow 326 and the air can be removed by a degasser (not shown). As with the sodium chloride container 303, the sodium bicarbonate container 302 can initially be nearly completely filled with sodium bicarbonate solids. The sodium bicarbonate container 302 can be filled only partially with water. As sodium bicarbonate concentrate is metered out of the sodium bicarbonate container 302 during use, additional fluid can be introduced into the sodium bicarbonate container 302, dissolving some of the remaining sodium chloride solids in the bottom section 320 of the container 302, so that the sodium bicarbonate solution remains approximately saturated.

Figure 6:
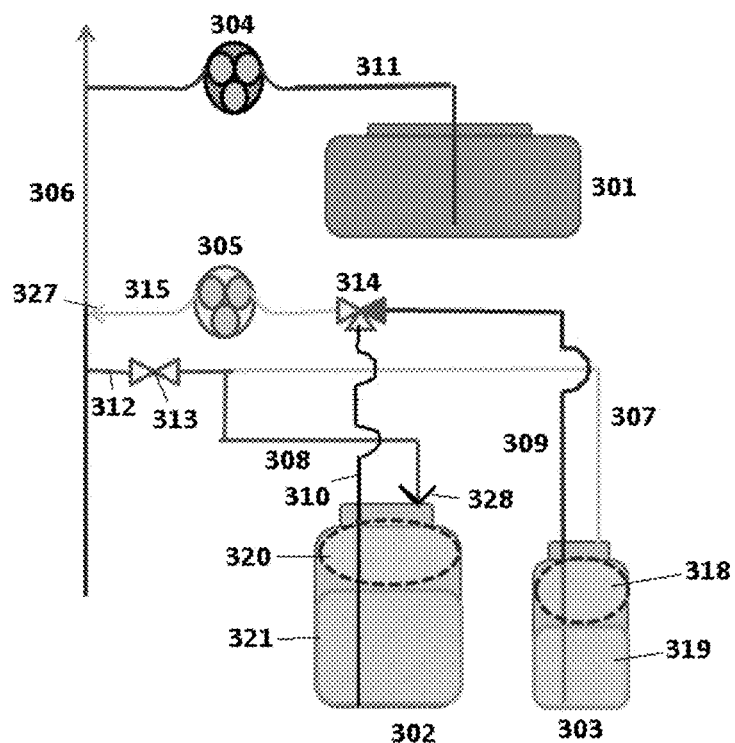
FIG. 6 shows a flow path of the connectors, pumps and valves in an infusate caddy using one two-way valve and one three-way valve during priming of dialysis system with sodium bicarbonate.

FIG. 6 shows the same system configured for moving the sodium bicarbonate solution from the sodium bicarbonate container 302 into the dialysate flow loop 306. Pump 305 can again be reversed, so fluid moves from the sodium bicarbonate container 302 into the dialysate flow loop 306. The sodium bicarbonate solution can travel through second fluid line 310, second valve 314 and then seventh fluid line 315 as represented by arrow 327. Fluid from the dialysate flow loop 306 can be pumped through sixth fluid line 312 and first valve 313 into the sodium bicarbonate container 302, by fifth fluid line 308 as shown by arrow 328. The sodium bicarbonate solution can enter the dialysate flow loop 306, and combine with the sodium chloride solution moved previously to create a dialysate with a desired sodium chloride and sodium bicarbonate concentration. Concentration sensors, such as conductivity sensors or pH sensors, can be included to ensure that the fluid in the dialysate flow loop 306 has the desired sodium bicarbonate concentration.

The amount of water moved into the sodium bicarbonate container and sodium chloride container to dissolve the sodium bicarbonate solids and sodium chloride solids can depend on the needs of the system and patient. Between 10 mL and 500 mL of water can be added to the sodium chloride container in the process illustrated in FIG. 3. The concentrate of sodium chloride produced can be around 5.5 M. For systems with a small dialysate flow path, such as 0.5 L, only about 15 mL of sodium chloride concentrate or less will be needed to prime the entire system. For larger systems, and for priming of sorbent cartridges, flush reprocessed dialyzers and for providing a fluid bolus to a patient, large amounts of sodium chloride may be necessary, requiring up to 500 mL of the sodium chloride concentrate. The sodium chloride container can have a volume of between 15 and 500 mL. Similarly, between 10 mL-4,000 mL of sodium bicarbonate concentrate may be required for the process illustrated in FIG. 5, and the sodium bicarbonate container can have a volume of between 10 mL and 4,000 mL. A system with a small dialysate flow path may only require about 10 mL of sodium bicarbonate concentrate for priming. However, for larger systems, and if the patient requires additional bicarbonate to correct acidosis, a large amount of sodium bicarbonate concentrate may be necessary.

During dialysis, second valve 314 as shown in FIGS. 3-6 can be selected opened and/or closed between the sodium chloride container 302 and sodium bicarbonate container 303 to selectively meter concentrated sodium chloride or sodium bicarbonate solution into the dialysate flow loop 306. The pump 305 can be cleared of any concentrated solution when switching between sodium bicarbonate and sodium chloride addition. To clear the pump 305 of concentrated solution, the pump can be reversed to draw an amount of fluid from the dialysate flow loop 306 into the fourth fluid line 309 or sodium second fluid line 310 to wash the pump 305 of any concentrated solution left in the lines immediately adjacent to the pump 305. The second valve 314 can then be switched to change the concentrate being added, adding no additional concentrate that may have been left in the lines. Pump 304 can be used during dialysis to add cation infusates or any other treatment solutes from the cation infusate container 301 into the dialysis flow loop 306 by third fluid line 311.

Figure 7A:
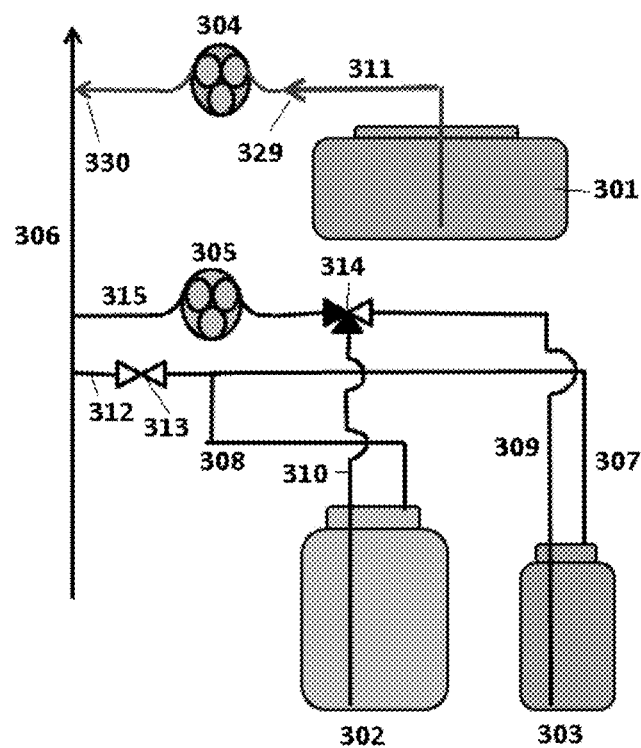
FIG. 7a shows a flow path of the connectors, pumps and valves in an infusate caddy using a two-way valve and a three-way valve controlling the clearing of disinfection solution from cation infusate lines.

A disinfectant such as citric acid can remain in the fluid lines of the dialysis machine and the user can install and connect the caddy before the citric acid is flushed from the fluid lines of the dialysis machine. FIGS. 7a-7d show a process of removing the disinfection solution prior to priming the system with the fluids from the caddy containers. FIG. 7a illustrates how a disinfectant solution can be moved from line 311 and pump 304 into the main dialysate flow loop 306 before the cation infusate container 301 is primed. The operation pumps the disinfectant solution by action of pump 304 into the dialysate flow loop 306, as illustrated by arrows 329 and 330, where the disinfection solution can be drained and flushed from the fluid pathways of the dialysis machine (not shown).

Figure 7B:
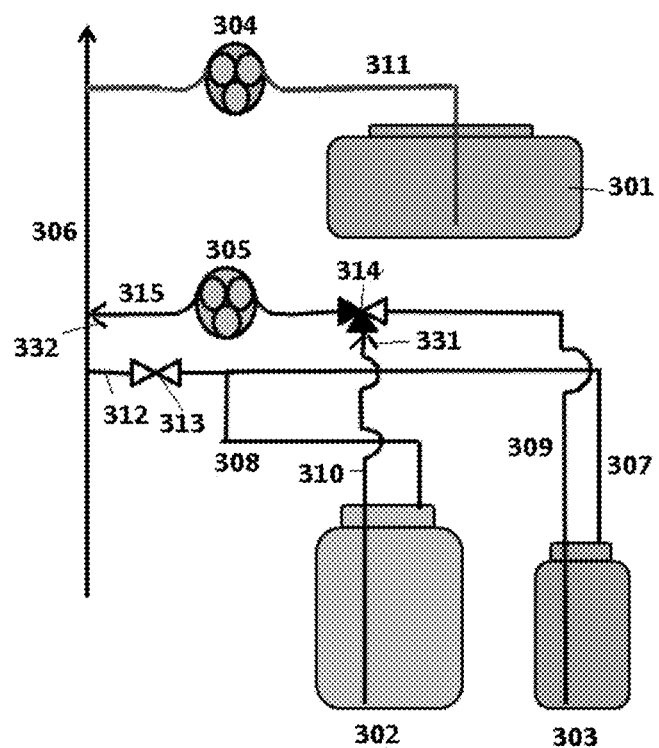
FIG. 7b a flow path of the connectors, pumps and valves in a infusate caddy using a two-way valve and a three-way valve controlling the clearing of disinfection solution from sodium bicarbonate lines.

FIG. 7b illustrates how a disinfectant solution can be moved from second fluid line 310, seventh fluid line 315 and pump 305 into the main dialysate flow loop 306. The operation pumps the disinfectant solution by action of pump 305 into the dialysis flow loop 306 as shown by arrow 332, where the disinfection solution can be drained and flushed from the fluid pathways of the dialysis machine (not shown). During the operation, air from the sodium bicarbonate container 302 can flow into the lines through second valve 314, as shown by arrow 331.

Figure 7C:
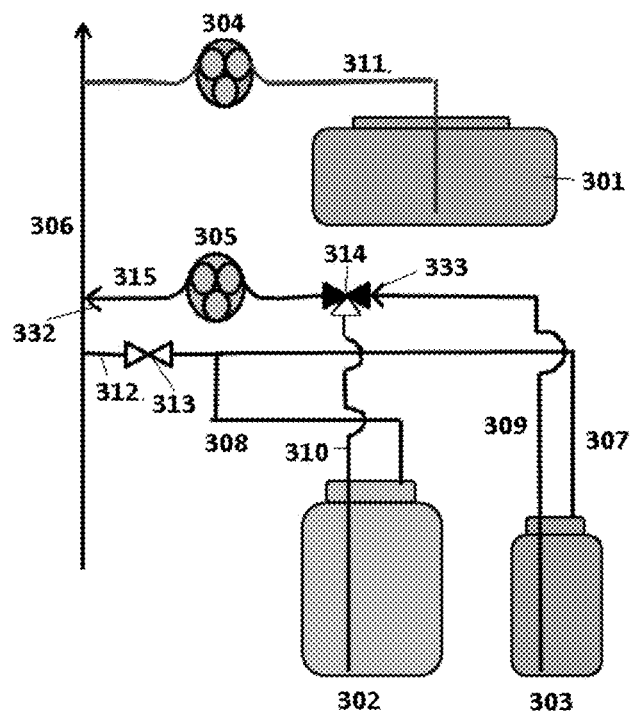
FIG. 7c a flow path of the connectors, pumps and valves in a infusate caddy using a two-way valve and a three-way valve controlling the clearing of disinfection solution from sodium chloride lines.

FIG. 7c illustrates how a disinfection solution can be moved from fourth fluid line 309, seventh fluid line 315 and pump 305 into the main dialysis flow loop 306. The operation pumps the disinfectant solution by action of pump 305 into the dialysis flow loop 306 as shown by arrow 332, where the disinfection solution can be drained and flushed from the fluid pathways of the dialysis machine (not shown). By switching second valve 314 from the sodium chloride container 303, air can flow into the lines through second valve 314, as shown by arrow 333.

Figure 7D:
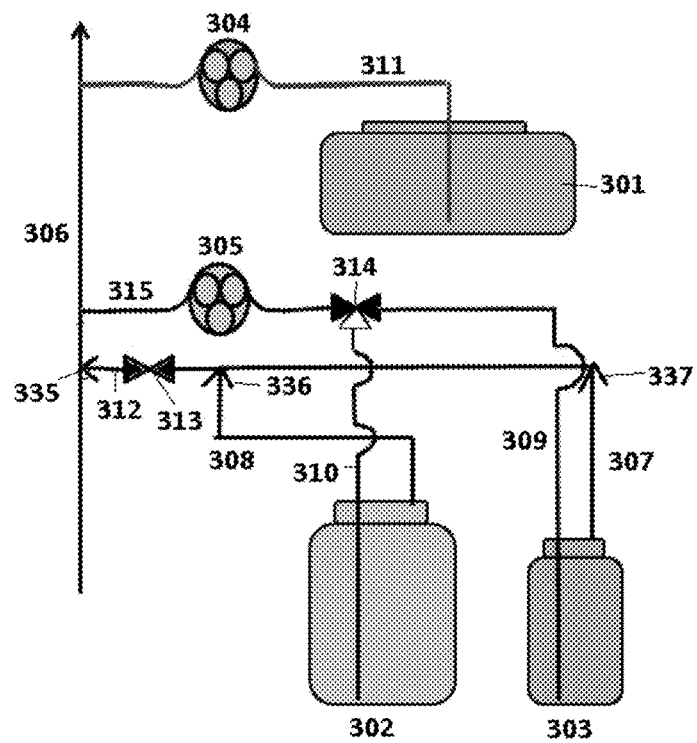
FIG. 7d a flow path of the connectors, pumps and valves in a infusate caddy using a two-way valve and a three-way valve controlling the clearing of disinfection solution from sodium chloride and sodium bicarbonate lines.

FIG. 7d shows how a disinfectant solution can be moved from fifth fluid line 308, first fluid line 307, first valve 313 and sixth fluid line 312 into the main dialysis flow loop 306. A pump (not shown) in fluid communication with the main dialysis flow loop line 306 is operated to evacuate the liquid from dialysate flow loop line 306 and create a negative pressure in dialysate flow loop line 306. After the negative pressure is created in dialysate flow loop line 306, first valve 313 is opened to allow the disinfectant to drain into the main dialysis flow loop line 306, as shown by arrow 335, from first fluid line 307 and second fluid line 308 as shown by arrows 337 and 336, where the disinfection solution can be drained and flushed from the fluid pathways of the dialysis machine (not shown).

Any of the lines, valves and pumps can be of any type known in the art. Any of the valves described as 2-way, 3-way or 4-way valves can be replaced with different types of valves or valve assemblies to accomplish the same functions. One skilled in the art will understand that the same steps described for the caddy configuration shown in FIGS. 3-7 can prime the containers and dialysis system with the configurations shown in FIGS. 1 and 2.

Figure 8:
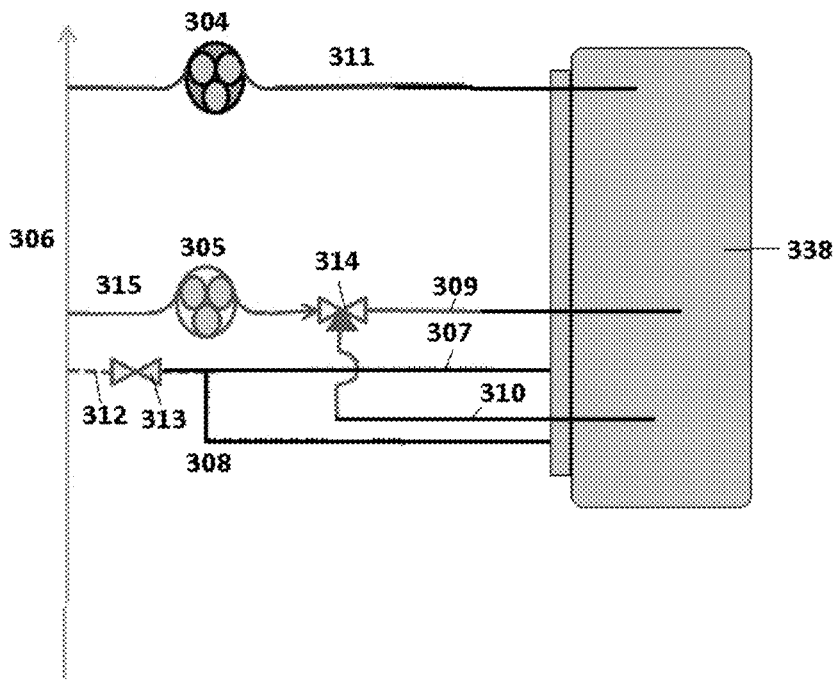
FIG. 8 shows a flow path of the connectors, pumps and valves in an infusate caddy configured for priming the system with disinfectant.

FIG. 8 shows the same system configured to prime the system for disinfection. Components with the same reference numbers in FIG. 8 as in FIGS. 3-7 correspond to the same components. The system in FIG. 8 is the same system as in FIGS. 3-7, redrawn for simplicity. The infusate caddy can include a disinfection container 338 that can be connected to the caddy and dialysis machine connectors when the caddy is placed in a disinfection configuration. As illustrated in FIG. 8, the fluid lines from the dialysis machine can be connected to disinfection container 338. Fluid line 311 and pump 304 can be used to pump disinfectant from the disinfectant container 338 into fluid line 311 and dialysate flow loop line 306 in order to prime the entire dialysis system with disinfectant. Similarly, pump 305 can be used to move disinfection solution from the disinfection container 338 into the dialysate flow loop line 306 through lines 307, 308, 309 and 310. Valves 314 and 313 can be switched as necessary to ensure that the disinfection solution reaches all fluid lines in the system. The disinfection solution can be recirculated through the disinfection container 338 and the dialysis system.

Figure 18:
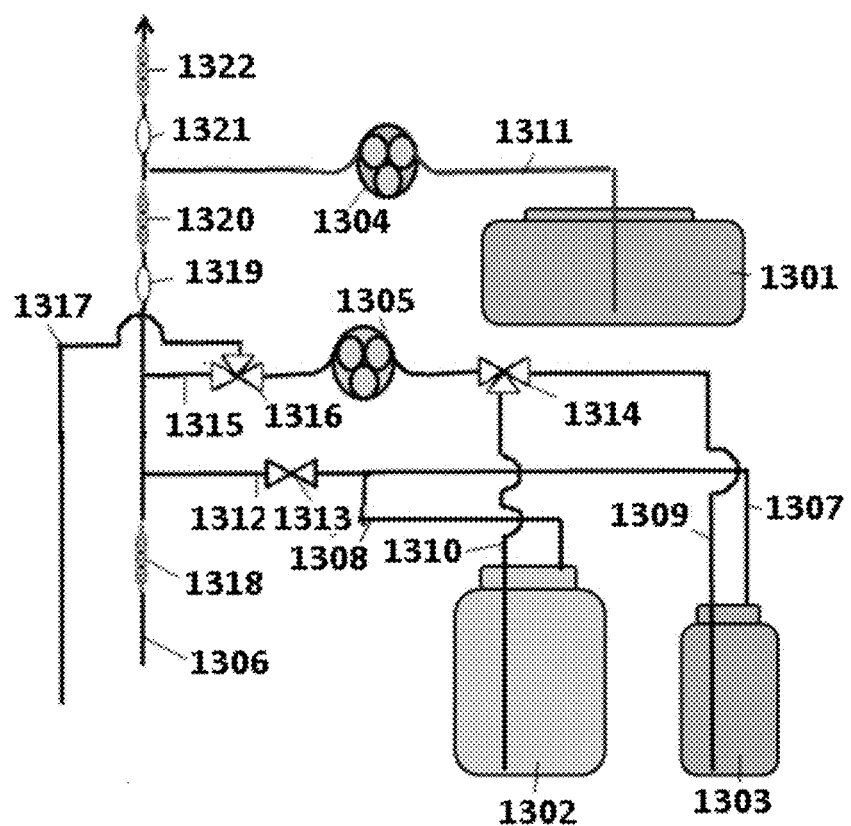
FIG. 18 shows a caddy configuration with a two-way valve and two three-way valves.

FIG. 18 illustrates a configuration for an infusate caddy utilizing and additional three-way valve 1316. The infusate caddy can contain a cation infusate container 1301, a sodium bicarbonate container 1302, and a sodium chloride container 1303, each of which can contain a solid source or a concentrate. Sodium chloride container 1303 can be connected to fluid lines 1307 and 1309. Fluid line 1307 can connect the sodium chloride container 1303 to valve 1313. Valve 1313 can also connect to fluid line 1312, which in turn connects to the main dialysate flow path 1306 allowing fluid from the dialysate flow path 1306 to enter the sodium chloride container 1303. Fluid line 1309 can connect to valve 1314, which also connects to valve 1316 downstream of pump 1305. Pump 1305 can control the movement of fluid through line 1309 and valve 1316. Valve 1316 can be operated to direct fluid into the main dialysate flow path 1306 during treatment by fluid line 1315, or alternatively to direct fluid through fluid line 1317 to a separate portion of the dialysate flow path 1306. As described, directing sodium chloride and sodium bicarbonate upstream of a sorbent cartridge (not shown in FIG. 18) can reduce the time necessary for priming the dialysis machine. Valve 1316 allows the sodium chloride and sodium bicarbonate to be pumped either upstream or downstream of the sorbent cartridge during priming and treatment, respectively.

Sodium bicarbonate container 1302 can be connected to fluid lines 1310 and 1308. Fluid line 1308 can also connect to valve 1313 and can allow fluid from the dialysate flow path 1306 to enter the sodium bicarbonate container 1302. Fluid line 1310 can also connect to valve 1314. Cation infusate container 1301 can be connected by fluid line 1311 to the main dialysate flow path 1306. Pump 1304 can control the movement of fluid through line 1311.

Either or both of pumps 1304 and 1305 can be capable of moving fluid bi-directionally to move fluid from the containers within the infusate caddy to the main dialysate flow loop 1306, or from the main dialysate flow loop 1306 to any of the containers within the infusate caddy.

During treatment, various sensors determine the concentration of sodium chloride, sodium bicarbonate, and cations added to the dialysate flow path 1306 from the caddy containers. Conductivity sensor 1318 can determine the conductivity of the dialysate prior to addition of sodium bicarbonate, sodium chloride, or other cations. Based on the conductivity detected by conductivity sensor 1318, the amount of each fluid that needs to be added to the dialysate can be determined. Conductivity sensor 1320, located downstream of fluid line 1315, determines the conductivity of the dialysate after addition of sodium bicarbonate, and ensures that the correct amount of sodium bicarbonate is added to the dialysate. Static mixer 1319 ensures complete mixing of the added sodium bicarbonate and the dialysate for accurate measurements by conductivity sensor 1320. Conductivity sensor 1322, located downstream of fluid line 1311, determines the conductivity of the dialysate after addition of the cation infusates, and ensures that the correct amount the cations is added to the dialysate. Conductivity sensor 1322 also provides a final check of the dialysate conductivity prior to the dialysate entering the dialyzer (not shown in FIG. 18). If the detected conductivity is outside of a predetermined range, the system can provide an alert, shutdown, or bypass the dialyzer to avoid delivering an unsafe dialysate to the patient. Static mixer 1321 ensures complete mixing of the added cation infusates and the dialysate for accurate measurements by conductivity sensor 1322. The static mixers and sensors illustrated in FIG. 18 can be included in any of the described caddy configurations.

Figure 19:
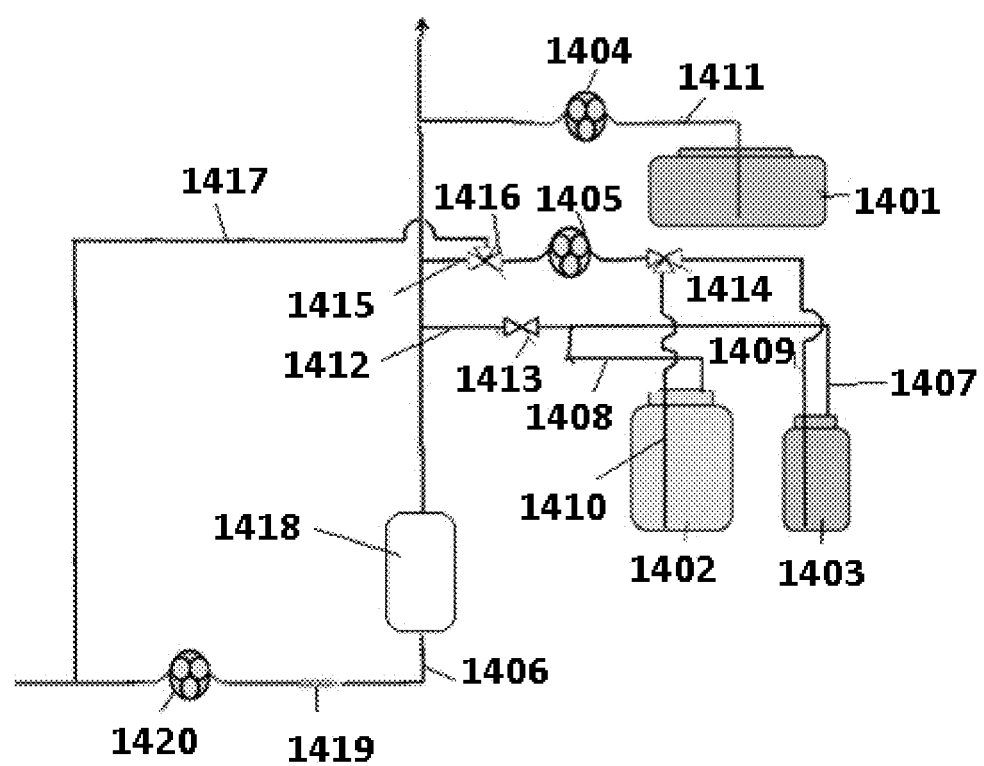
FIG. 19 shows a portion of a dialysate flow path connected to containers in a caddy.

FIG. 19 illustrates a simplified portion of a dialysate flow path 1406 using the caddy configuration illustrated in FIG. 18. Sodium chloride container 1403 can be connected to fluid lines 1407 and 1409. Fluid line 1407 can connect the sodium chloride container 1403 to valve 1413. Valve 1413 can also connect to fluid line 1412, which in turn connects to the main dialysate flow path 1406 allowing fluid from the dialysate flow path 1406 to enter the sodium chloride container 1403 for priming of the sodium chloride container 1403. Fluid line 1409 can connect to valve 1414, which also connects to valve 1416 downstream of pump 1405. Pump 1405 can control the movement of fluid through line 1409 and valve 1416. Valve 1416 can be selectively openend and closed to direct fluid into the main dialysate flow path 1406 during treatment by fluid line 1415, or alternatively to direct fluid through fluid line 1417 to a separate portion of the dialysate flow path 1406.

Sodium bicarbonate container 1402 can be connected to fluid lines 1410 and 1408. Fluid line 1408 can also connect to valve 1413 and can allow fluid from the dialysate flow path 1406 to enter the sodium bicarbonate container 1402. Fluid line 1410 can also connect to valve 1414. Cation infusate container 1401 can be connected by fluid line 1411 to the main dialysate flow path 1406. Pump 1404 can control the movement of fluid through line 1411.

As described, valve 1416 allows fluid to be directed to the dialysate flow path 1406 upstream of sorbent cartridge 1418. To reuse a dialyzer (not shown in FIG. 19), the dialyzer must be sterilized with a disinfectant solution. The disinfectant solution must then be flushed out of the dialyzer and dialysate flow path 1406 by pumping fluid through the dialysate flow path 1406. The sorbent cartridge 1418 must then be flushed, drained, conditioned with sodium bicarbonate and primed with sodium chloride. Without valve 1416, sorbent cartridge 1418 would fill with water prior to conditioning. The sorbent cartridge 1418 would then need to be flushed with additional sodium bicarbonate solution that has passed through the entire dialysate flow path 1406 for conditioning. By directing the sodium bicarbonate through fluid line 1417 upstream of the sorbent cartridge 1418, only fluid with sodium bicarbonate enters the sorbent cartridge 1418, reducing the time necessary for conditioning of the sorbent cartridge 1418. After conditioning, the sorbent cartridge 1418 is primed with a sodium chloride solution. By directing the sodium chloride through fluid line 1417 upstream of the sorbent cartridge 1418, only fluid with sodium sodium chloride enters the sorbent cartridge 1418, reducing the time necessary for priming of the sorbent cartridge 1418. The total time for conditioning and priming the system can be reduced by as much as 5-15 minutes by directing fluid upstream of the sorbent cartridge with valve 1416. Pump 1420 provides the driving force for conveying dialysate and priming solution through the dialysate flow path 1406. Conductivity sensor 1419 detects the conductivity of the fluid prior to entering the sorbent cartridge 1418. The conductivity of the fluid, along with the flow rate of the fluid, allows determining of the amount of bicarbonate and sodium chloride pumped through the dialysate flow path 1406, allowing closed loop control during priming and flushing. One of skill in the art will understand a valve similar in function to valve 1416 can be included in any of the described caddy configurations.

Figure 9:
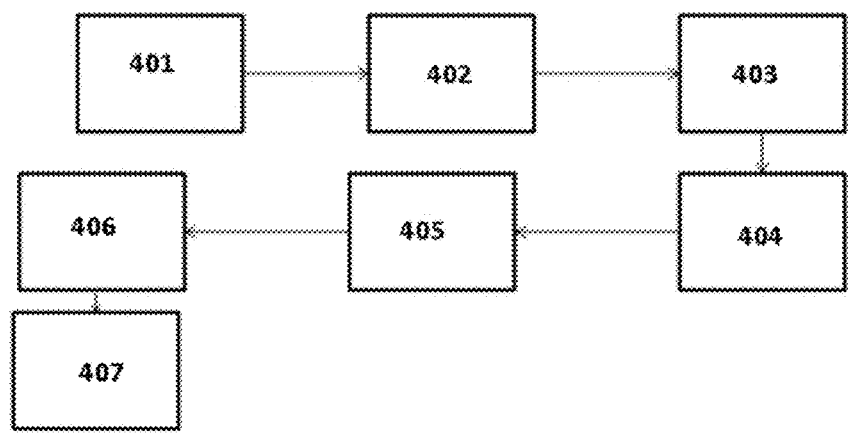
FIG. 9 is a flow chart showing the steps of priming an infusate caddy and priming a dialysis system with fluids from the infusate caddy.

FIG. 9 is a flow chart showing the steps used to prime the components of an infusate caddy, and to use the infusate caddy to prime a dialysis system and create dialysate for dialysis. In step 401, the infusate caddy is installed and connected to a dialysis machine. Installing the infusate caddy can include connecting each of the containers within the infusate caddy to particular connectors on a dialysis machine. The infusate caddy can contain one or more containers for dialysis, including a sodium chloride container, a sodium bicarbonate container and a cation infusate container. The infusate caddy can be configured so each container within the infusate caddy can be connected to a particular connector on the dialysis machine. Using the infusate caddy can ensure that each of the containers is connected to a dialysate flow loop at a correct location.

A disinfectant solution, such as a citric acid solution, can remain in the fluid lines of the dialysis machine and the user can install and connect the caddy before the citric acid is flushed from the fluid lines of the dialysis machine. In step 402 the residual disinfectant can be removed from the fluid lines of the dialysis machine that connect to the caddy.

Any of the containers in the infusate caddy can initially contain a solid source of the particular material to be added to the dialysate flow loop during priming or use of the dialysis system. Before adding fluids to the dialysis system, liquid can be added to the infusate containers to dissolve the solids to produce a concentrate that can be metered into the dialysate fluid pathway of the dialysis machine. Optionally, the infusate containers can contain solutes having the desired solutes. In step 403, fluid from the dialysis system is added to a sodium chloride container to dissolve a portion of the sodium chloride until an approximately saturated solution is produced to generate a sodium chloride solution of known concentration, as illustrated in FIG. 3. In step 404, the sodium chloride solution can be added to the dialysate flow loop to prime the dialysate flow loop with a sodium concentration suitable for use in dialysis, as described in FIG. 4.

In step 405, fluid from the dialysate flow loop can be added to a sodium bicarbonate container to dissolve a portion of the solid sodium bicarbonate until an approximately saturated solution is produced to generate a sodium bicarbonate solution of a known concentration, as described in FIG. 5. In step 406, the sodium bicarbonate solution can be added to the dialysate flow loop to create a dialysate with a specified sodium bicarbonate and sodium chloride solution suitable for use in dialysis. The operation of the pumps and valves described herein can be set to result in the specified sodium bicarbonate and sodium chloride solution, as described in FIG. 6.

Optionally, in step 407, fluid can be added from the dialysate flow loop to a cation infusate container in the infusate caddy, to dissolve a solid source of cation infusates and create an infusate solution of a known concentration. The infusates, or any other treatment solutes, can be added to the dialysate flow loop as needed during dialysis. Step 407 can be performed before or after step 404, step 405 or step 406. Further, the bicarbonate concentrate and the cation infusate can be metered into the dialysate flow loop concurrently.

The pumps and valves can be operated by an electronic control system. The electronic control system can be programmed to carry out the steps illustrated in FIGS. 3-8. The control system can be programmed to move a predetermined amount of fluid into and out of the containers described, allowing the control system to control the amount of each of the solutes in the dialysate during a dialysis session. After the infusate caddy is seated or attached to the dialysis system, the system can be flushed of any fluid, filled with water, and then primed. The valves connecting the dialysate flow loop to the caddy containers as illustrated in FIGS. 1-8 can be closed to the dialysate flow loop, such that fluid cannot move from the dialysate flow loop into the sodium bicarbonate, sodium chloride or cation infusate containers, keeping citric acid or other disinfectants originally present in the dialysate flow loop from contaminating the sodium chloride or sodium bicarbonate solutions.

Infusate Caddy

Figure 10:
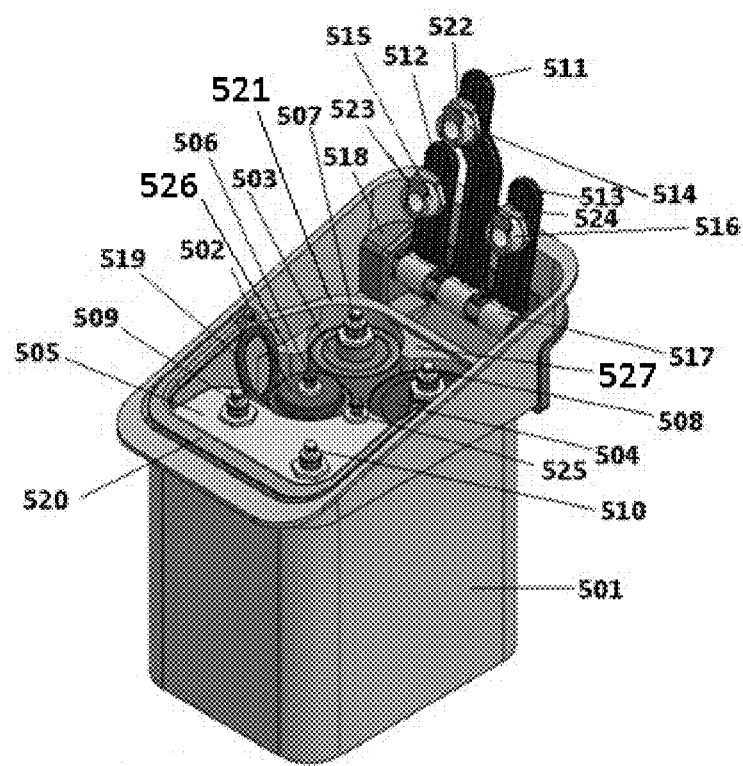
FIG. 10 shows an infusate caddy containing solute containers in a portion of a dialysis machine.

The infusate caddy can be arranged as shown in FIG. 10. The body of the infusate caddy 521 can be configured to contain the ion sources, infusates, electrolytes, other solutes, or combinations thereof needed for dialysis. The body of the infusate caddy 521 can be configured to contain one or more infusate containers that contain the necessary ion sources, infusates, electrolytes, other solutes, or combinations thereof, needed for dialysis. The caddy 521 can have a fitting feature such as a protrusion, indentation, groove, or ridge positioned on the caddy 521 wherein the fitting feature has any shape, size, or geometry that is complementary to a corresponding geometry, a corresponding size, or a corresponding shape on the infusate containers. For example, the fitting feature can be positioned on an interior surface in a receiving compartment of the caddy 521, wherein the receiving compartment is designed to receive an infusate container designed to occupy a unique position inside the caddy 521. In one-non-limiting example, a curved wedge protrusion 526 and a curved wedge protrusion 527 are positioned on the walls of the receiving compartment of the infusate caddy 521. The respective radii of the cation infusate container 502 and the sodium bicarbonate container 503 can be sized to be positioned appurtenant to curved wedge protrusion 526. Similarly, the respective radii of sodium bicarbonate container 503 and sodium chloride container 504 can be sized to be positioned appurtenant to curved wedge protrusion 527. Each of the infusate containers can have unique shape and/or size to ensure that the infusate container is not inadvertently placed in the wrong receiving compartment of the infusate caddy 521. Optionally, a corresponding fitting feature can be positioned on a surface of the infusate container to ensure that the infusate container correctly mates or connects to the infusate container at a unique position when placed inside the receiving compartment of the caddy 521. The fitting feature is not limited to merely protrusions, indentations, grooves, or ridges, and can include any size and/or shape of the receiving compartment. For example, a depth, incline, or diameter of the receiving compartment can serve as a fitting feature and serve as a complementary surface. In such a case, the corresponding fitting feature can be an exterior surface shape, diameter, length, or curvature of an infusate container designed to fit inside the caddy 521. Each of the infusate containers can have unique shapes and size to ensure that the infusate container is not inadvertently placed in the wrong receiving compartment.

The caddy 521 can have fitting features on an exterior surface for the caddy 521 to fit within a receiving compartment on a dialysis machine 501. The ion sources and infusates sources can include cation infusate container 502, sodium bicarbonate container 503 and sodium chloride container 504. One skilled in the art will understand that the caddy 521 can be configured to contain any number of different combinations, shapes, and sizes of infusate containers than those shown in FIG. 10. The fitting feature can also include a visual indicator of the position of each of the containers, such as by labeling or color coding to indicate the correct position of each of the containers. For example, a label or color code can be affixed to indicate the correct position of each of the infusate containers. The correct position of the sodium bicarbonate container can be blue, and the sodium bicarbonate container can also be blue. The correct position for the cation infusate container can be red, and the cation infusate container can also be red. The user can simply match the blue container to the blue position in the caddy, and the red container to the red position in the caddy. One of skill in the art will understand that any color or visual coding system including letters and symbols can be used to indicate the correct position for each container. The fitting feature can also be non-mechanical means for ensuring complementary connection such as magnets placed at particular locations in the caddy 521. Multiple infusate sources can be used, or containers with other ions necessary for a dialysis session can be included. The caddy 521 can contain more or less than four infusate containers any of which can have the described fitting feature. Additional solute containers can contain an enzyme, such as urease, for addition to a sorbent cartridge, and other solutes for removal or control over concentrations of solutes in the dialysate, such as barium carbonate for control over sulfate in the dialysate. Any number of infusate containers can be connected to any number of connectors. Each infusate can be in a separate container, such as a magnesium infusate container, a potassium infusate container and a calcium infusate container. Any of the infusate containers shown in the figures can be eliminated from the caddy. Any one or more of the containers within the caddy 521 can have a handle for easy removal of the container, such as handle 519 on cation infusate container 502. The caddy 521 can include fitting features that ensure specific containers can only occupy specific positions within the caddy. The caddy can contain more or less than four containers. Any combination of fitting features can be used together. For example, an infusate container can have a color code, a magnet of proper polarity, and a groove for proper mating to a corresponding receiving compartment.

The body of the caddy 521 can be configured to contain one or more infusate containers that contain ion sources, infusates, electrolytes, other solutes, or combinations thereof, needed for dialysis. The caddy 521 can have a fitting feature such as a protrusion, indentation, groove, or ridge positioned on the caddy 521 wherein the fitting feature has any shape, size, or geometry that is complementary to a corresponding fitting feature. For example, the fitting feature can be positioned on an interior surface in a receiving compartment of the caddy 521, wherein the receiving compartment is designed to receive an infusate container designed to occupy a unique position inside the caddy 521. The corresponding fitting feature can then be positioned on a surface of the infusate container to ensure that the infusate container correctly mates or connects to the infusate container at a unique position when placed inside the receiving compartment of the caddy 521. The fitting feature is not limited to merely protrusions, indentations, grooves, or ridges, and can include any size and/or shape of the receiving compartment. For example, a depth, incline, or diameter of the receiving compartment can serve as a fitting feature and serve as a complementary surface. In such a case, the corresponding fitting feature can be an exterior surface shape, diameter, length, or curvature of an infusate container designed to fit inside the caddy 521. Each of the infusate containers can have unique shapes and size to ensure that the infusate container is not inadvertently placed in the wrong receiving compartment.

The fitting feature can also include a visual indicator. For example, a label or color code can be affixed to indicate the correct position of each of the containers. The correct position of the sodium bicarbonate container can be blue, and the sodium bicarbonate container can also be blue. The correct position for the cation infusate container can be red, and the cation infusate container can also be red. The user can simply match the blue container to the blue position in the caddy, and the red container to the red position in the caddy. One of skill in the art will understand that any color or visual coding system including letters and symbols can be used to indicate the correct position for each container. The fitting feature can also be non-mechanical means for ensuring complementary connection such as magnets placed at particular locations in the caddy 521. Any combination of fitting features can be used together. For example, an infusate container can have a color code, a magnet of proper polarity, and a groove for proper mating to a corresponding receiving compartment.

Any one or more of the containers within the caddy 521 can have a handle for easy removal of the container, such as handle 519 on cation infusate container 502. Each of the containers can include a fluid connector for fluid connection to the dialysis system, such as connector 506 on cation infusate container 502, connector 507 on sodium bicarbonate container 503 or connector 508 on sodium chloride container 504. The fluid connectors may have affixed thereon, or may itself, be a fitting feature, as described herein, such that connectors can connect to a particular infusate container having a corresponding fluid fitting for placement of the infusate container into the caddy 421 at the appropriate location. One or more valves (not shown in FIG. 10) can be included on the connectors to control the movement of fluid from the containers, through the connectors and into the dialysis system. One or more valves may be included on connectors in the dialysis system fluidly connected to the connectors 506, 507, and 508 in order to control the movement of fluid from the containers through the connectors and into the dialysis system. Check valves (not shown) or a poppet type valve can be included on connectors 506, 507, and 508 to limit direction of flow to be unidirectional, or to prevent spillage when the connectors are disengaged. The valves may be 2-way, 3-way, 4-way or any other type of valve. The valves may be configured such that fluid can move through the connectors bi-directionally, that is, fluid may move from the containers into the dialysis system, or fluid may move from the dialysis system and into the containers. The connectors can be configured so both gas and liquid may move through the valves and into or out of the containers.

The fluid connectors can be coaxial wherein a first fluid flow path at a first radius is concentric to second flow path having a radius greater than the first flow path. Coaxial connectors allow simultaneous fluid ingress and fluid egress from the container through a single connector. Using coaxial connectors allows solid solute sources to be used in each of the containers because fluid can be directed into the containers to dissolve the solid solute, creating a solute solution, and then the solute solution can be added into the dialysis circuit. Using coaxial connectors also allows pressure equalization in the containers as fluid is added or removed, because gas can also be added or removed from the container at the same time.

The infusate caddy 521 can also include a disinfection container, such as citric acid container 505. After dialysis is complete, the user can disconnect or remove sodium chloride container 504, sodium bicarbonate container 503, and cation infusate container 502, and connect the dialysis machine to citric acid container 505 through connectors 509 and 510. Citric acid can be moved from the citric acid container 505 into the fluid lines of the dialysis system to disinfect the system and prepare the system for the next use. The infusate caddy 521 can be moved into a disinfection configuration as described in order to place citric acid container 505 in position for connection to the dialysis machine.

The infusate containers can contain a solid material or solids that can be dissolved to create the appropriate solution. For example, sodium chloride container 504 can contain sodium chloride solids. Water may be added to the sodium chloride container 504 through connector 508 during the priming and set up of the dialysis system. Because the sodium container 504 contains an amount of sodium chloride solids when water is added to sodium chloride container 504, the resulting sodium chloride solution produced in sodium chloride container 504 will be approximately saturated and thus of a known concentration. The sodium chloride solution can then be used during dialysis. Similarly, the sodium bicarbonate container 503 can contain sodium bicarbonate solids and the cation infusate container 502 can contain a solid source of cations of a known mass, each of which can be dissolved with a known amount of water to create a fluid for dialysis. The cations can be present in cation infusate container 502 as a pre-mixed liquid which can be used in dialysis without additional water being added to cation infusate container 502 by the system.

The infusate caddy 521 can include caddy connectors for connection to the connectors on each of the containers in the caddy. As shown in FIG. 10, the caddy connectors can be included on paddles 511, 512, and 513. The caddy connectors can connect to dialysis machine connectors for addition of the solute solutions into the dialysis system. The caddy 521 may include means for securing each of the containers in the proper location within the caddy 521 for proper connection to the dialysis system. Furthermore, an exterior surface of the caddy connectors can have a fitting feature to ensure proper mating to corresponding infusate container. For example, a first caddy connector can have a hexagonal-shape while a second caddy connector can have a circular-shape. The corresponding infusate containers can have surfaces matched to receive the hexagonal- or circular shaped caddy connectors. One skilled in the art will understand that additional solute containers can be included in the caddy, and that additional paddles and connectors can be included as necessary.

The caddy connectors need not be included on paddles and can be included on a length of hose, wherein the hose is fluidly connected to a dialysis flow path. The hose can be made of any material known in the art for use in dialysis systems, including silicone, reinforced silicone, or PVC. One skilled in the art will understand that other biocompatible materials can be used for the hose, and the hose is not limited to these materials. The hoses can be either flexible or semi-rigid, which would allow the hoses to move for connection to the containers in the caddy. The hoses can be sized and positioned such that each hose will only be able to connect with a single container within the caddy. For example, each hose may be positioned on a specific location with respect to the caddy, and each hose can be short enough so that the hose cannot reach any container not aligned with the specific location.

In FIG. 10, the locking means can be a paddle assembly 518. Each of the paddles 511, 512 and 513 in paddle assembly 518 can be lockable paddles and include a locking connector, such as caddy connector 514 on paddle 511, caddy connector 515 on paddle 512 and caddy connector 516 on paddle 513 configured to lock the infusate containers in place. The paddles 511, 512, and 513 can be rotate about a hinge 517. After the containers are properly placed within the caddy 521, the paddles of the distal end of the paddles can be lowered and connect to corresponding container connectors 506, 507, and 508 on the containers within the caddy 521. The configuration of assembly 528 and caddy 521 can ensure that the correct connectors will be aligned to the correct container to prevent connection errors by the user. The paddles of the paddle assembly 518 can be lowered by pivoting the paddles on hinge 517. The caddy connectors 514, 515, and 516 positioned on the distal end of the paddles can fit over the container connectors 506, 507, and 508, respectively. The caddy connectors 514, 515, and 516 can be tightened to lock the containers in place by twisting the paddle connectors 514, 515, and 516. Once tightened, the caddy connectors 514, 515, and 516 lock the containers in place, and thus will resist inadvertent disconnection. The paddle assembly 518 can include a locking mechanism (not shown), so that after the paddles are lowered and locked into place, the paddles will resist inadvertent in a vertical and/or lateral direction. The caddy connectors can include a locking mechanism 522 as shown on caddy connector 514, locking mechanism 523 as shown on caddy connector 515 and locking mechanism 524 as shown on caddy connector 516, each of which can lock the paddles on to the container connectors 506, 507, and 508.

The paddle assembly 518 may be constructed as part of the caddy 521. The paddle assembly 518 can be constructed such that when the containers are placed within the caddy 521, the paddles 511, 512, and 513 are aligned with the respective containers for connection to the caddy connectors 514, 515, and 516. The paddle assembly 518 can instead be constructed as part of the dialysis machine 501, separate from the caddy 521. When the caddy 521 is placed into the dialysis machine, the paddles 511, 512 and 513 will align with each of the container connectors. By placing the paddle assembly 518 on the dialysis machine, the containers can be arranged within the caddy so that when the caddy is rotated, citric acid container 505 is aligned with one or more paddles 511 for connection to the dialysis machine 501. By rotating the caddy 521 so the citric acid container 505 is aligned for connection to the dialysis machine, the caddy 521 can be placed in a disinfection configuration, allowing citric acid to be moved from the citric acid container 505 through the container connectors 509, 510, and 525, the caddy connectors 514, 515, and 516 on paddles 511, 512, and 513 and into the dialysis machine 501 for disinfection. The caddy 521 can include handle 520 for easy movement of the caddy 521. Citric acid container 505 can contain internal fluid pathways between any of connectors 509, 510, and 525 to allow a cleaning and/or disinfection solution to be recirculated through one or more of connectors 511, 512 and 513 by action of a single pump.

Figure 11:
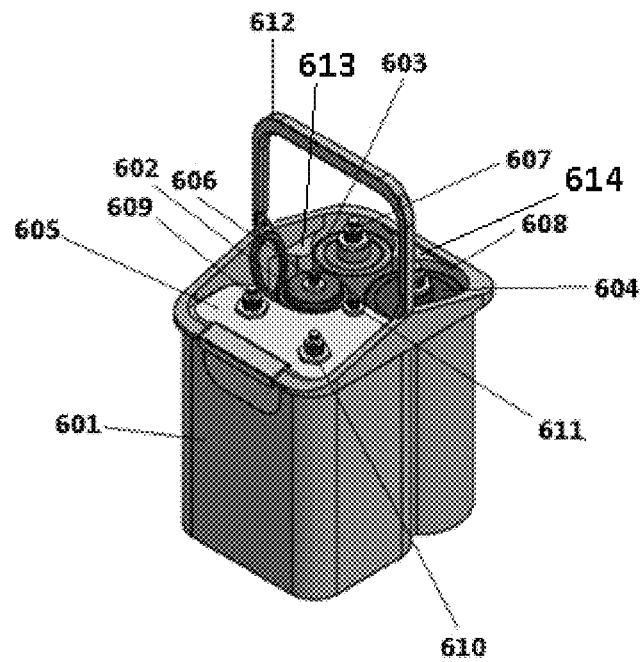
FIG. 11 shows an infusate caddy containing solute containers removed from a dialysis machine.

FIG. 11 shows an infusate caddy 601 removed from a receiving compartment of a dialysis machine. As in FIG. 10, the caddy 601 of FIG. 11 includes cation infusate container 602, sodium bicarbonate container 603 and sodium chloride container 604. Protrusion 613 and protrusion 614 can provide fitting features for the respective receiving compartments for each of the cation infusate container 602, sodium bicarbonate container 603 and sodium chloride container 604. A citric acid container 605 can be optionally added for disinfection after each dialysis session. In a preferred, non-limiting embodiment, an infusate caddy only contains cation infusate container 602, sodium bicarbonate container 603 and sodium chloride container, and does not include a citric acid container. Each of the cation infusate container 602, sodium bicarbonate container 603 and sodium chloride container 604 can be connected to a dialysis system by connectors 606, 607, and 608 respectively. In FIG. 11, the paddles as illustrated in FIG. 10 are attached to the dialysis machine, and not to the caddy 601. The paddles can be configured so that in the lowered state the paddles align with the connectors of the containers 602, 603 and 604. The caddy can be also configured in a disinfection configuration after use so that the paddles align with citric acid container 605, through connectors 609, 610 and 611. As shown in FIG. 11, the optional handle 612 can be raised for easy carrying of the caddy 601.

Figure 12:
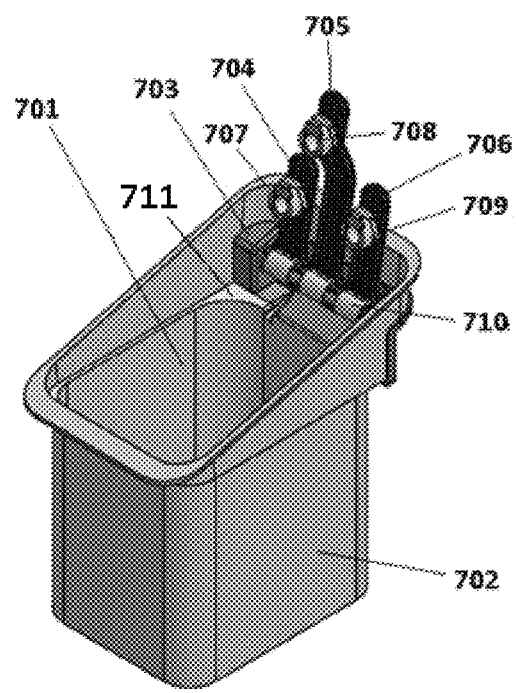
FIG. 12 shows an infusate caddy with no containers.

FIG. 12 shows a receiving compartment 701 and a paddle assembly 703 located at a top section of a dialysis machine 702 with the infusate caddy (now shown) removed. The infusate caddy can be removed to replace the containers, refill the containers, store the caddy, clean the caddy, clean the interior of the receiving compartment 701, or for any other reason. The caddy connectors 707, 708, and 709 can be disconnected from the corresponding container connectors as described. The containers, once the paddles 704, 705 and 706 of the paddle assembly 703 can be raised by pivoting on hinge 710, can be removed from the interior of the caddy 701. The receiving compartment 701 can be cleaned, and reused with the same or different infusate caddy having an appropriate fitting feature. Curved protrusion 711 can be positioned in at least one of the four corners of the interior of the receiving compartment 701 as a fitting feature for receiving an infusate caddy have a substantially rectangular shaped with curved corners. As described, the fitting feature can include protrusions, indentations, grooves, ridges, size and/or shape, a depth, incline, or diameter to provide complementary surface for an infusate caddy or position of the infusate caddy inside the receiving compartment 701.

Figure 13A:
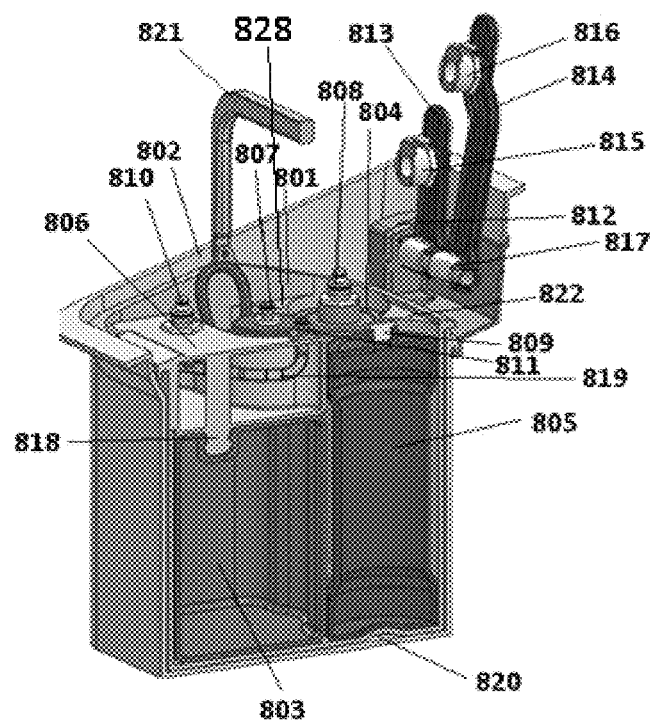
FIG. 13a shows a cut-away view of an infusate caddy containing solute containers in a dialysis machine configured to be used in dialysis.
Figure 13B:
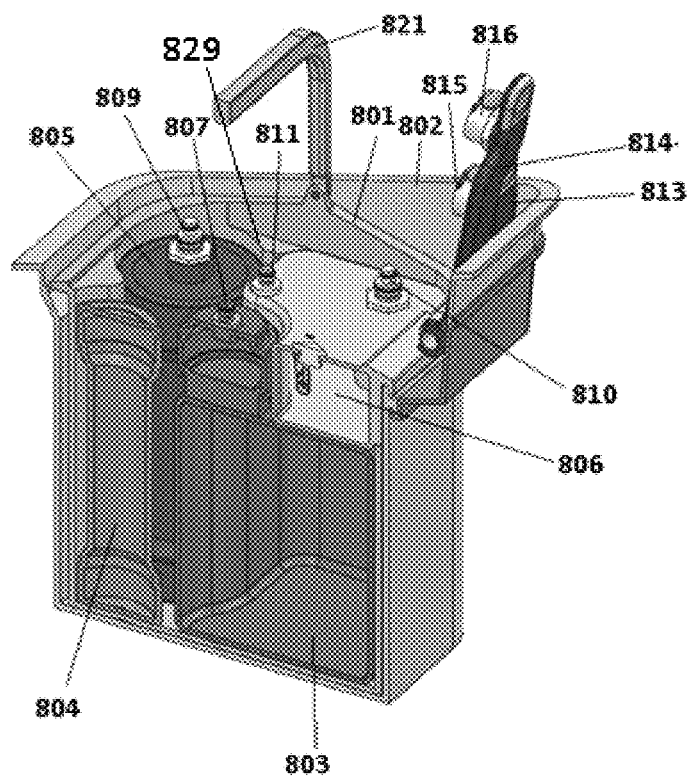
FIG. 13b shows a cut-away view of an infusate caddy containing solute containers in a dialysis machine configured to be used in disinfection.
Figure 13C:
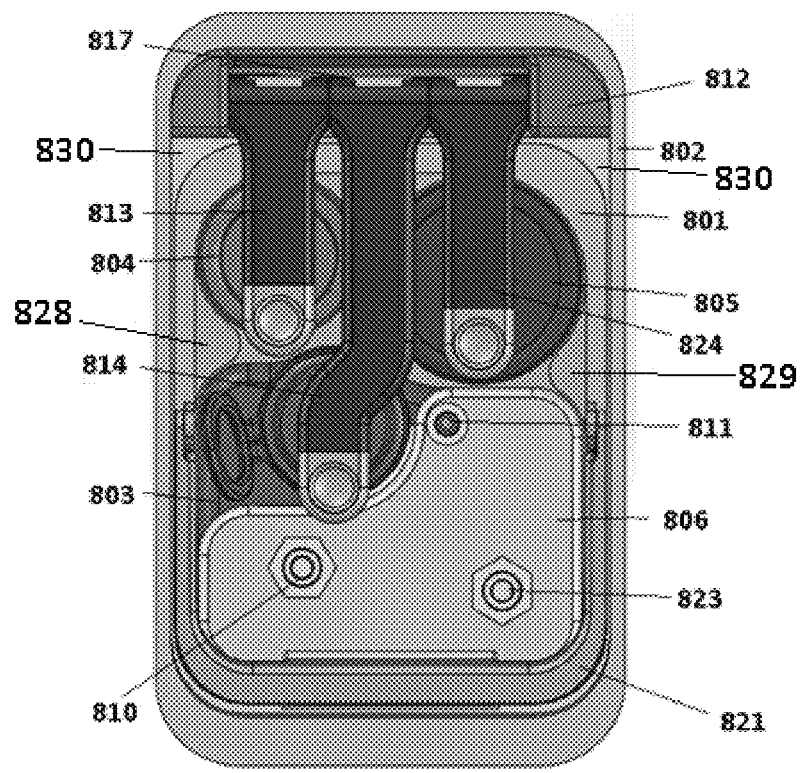
FIG. 13c shows a top view of an infusate caddy containing solute containers in a dialysis configuration.

FIGS. 13a and 13b show cutaway views of a caddy, while FIG. 13c shows a top view of a caddy. Components identified by the same reference numbers in FIGS. 13a, 13b and 13c correspond to the same components. FIG. 13a shows a caddy in a dialysis configuration, where the caddy 801 is configured in the receiving compartment 802 so the cation infusate container 803, sodium bicarbonate container 804, and sodium chloride container 805 are aligned with the paddles 813 and 814. Citric acid container 806 is not connectable to any paddle in the dialysis configuration of FIG. 13a. Container connector 807 on cation infusate container 803 and container connector 808 on sodium bicarbonate container 804 can connect to caddy connectors 815 on paddle 813 and caddy connector 816 on paddle 814. Container connector 809 on sodium chloride container 805 can also connect to a caddy connector (not shown in FIG. 13a). The paddles can be part of paddle assembly 812. To connect the containers to the paddles, the paddles can be rotated downward on hinge 817 and the caddy connectors 815 and 816 can connect to containers 803 and 804 respectively. As shown in FIGS. 13a and 13b, the caddy 801 and the containers within the caddy have one or more fitting feature to ensure the containers are connected to the correct paddle. The fitting features can also have the additional benefit of ensuring a tight fit within the caddy 801, and resist inadvertent movement. The one or more fitting features can ensure each container occupies a unique position within the caddy 801. Moreover, the interior of the caddy 801 can itself be a shaped fitting feature so each container can only be placed within a specific position or receiving compartment within the caddy 801. Fitting features can be included on any connection surface of the caddy, where any container contacts the interior of the caddy. The shape of a caddy surface base can include fitting feature protrusion 820, which is a protrusion on the base of the caddy 701. For example, sodium chloride container 805 can be designed with a corresponding complementary indentation, such as a similarly sized recess, while the other containers lack the complementary indentation. Container 805 will be the only container that can properly fit into the position in the caddy above the fitting feature of protrusion 820. Similarly, curved wedge protrusion 822 is disposed on side of the caddy 801 interior. The curved wedge protrusion 822 separates the sidewall of the caddy 801 interior into two sections. Sodium bicarbonate container 804 can be the only container with the proper size, shape, or geometry to fit within one of the sections on the sidewall, whereas sodium chloride container 805 can be the only container with the proper size, shape, or geometry to fit within the other section. Each container can be positioned in one particular location within the caddy 801. Any of the infusate containers themselves can have fitting features that ensure the proper arrangement of the containers within the caddy 801. In FIG. 13a, citric acid container 806 includes flange 818. Cation infusate container 803 has a corresponding position within the caddy 801. The citric acid container 806 can only be placed within the caddy 801 at the precise position above cation infusate container 803. By sizing and shaping the interior of the cavity and the containers, the containers can only be placed within the caddy 801 in a single arrangement. When the caddy 801 is attached to the receiving compartment 802, the containers and connectors line up with the proper paddles for connection to the dialysis system, ensuring that the proper solutes from the containers enter the dialysate flow path at the correct locations and that the proper pumps and valves are controlling the correct solute additions. Handle 821 can be included for easy of carrying and removal of the caddy 801 from the receiving compartment 802. During use, fluid lines, such as line 819 in citric acid container 806, can move fluids from the containers into the paddles.

The fitting features can include specific types of connectors on the containers and on the paddles or specific locking mechanisms on the paddles adapted for connection to a specific container. For example, connector 807 can be of a specific size, shape, geometry or type, while connector 808 can be of a different size, shape, geometry or type. Correspondingly, caddy connector 816 can be of a complementary size, shape, geometry or type to connector 807, while caddy connector 815 can be of a complementary size, shape, geometry or type to connector 808. In use, caddy connector 816 will only be able to lock onto and form a fluid connection with connector 807, while caddy connector 815 will only be able to lock onto and form a fluid connection with connector 808. That is, each paddle can include a locking mechanism adapted for a particular container ensuring that the respective containers are connected to the correct paddles for use in dialysis.

FIG. 13*b* shows the infusate caddy 801 in a disinfection configuration. The infusate caddy 801 can be placed in a disinfection configuration by rotating the caddy 801 so that the paddles 813 and 814 align with connectors 809 and 810 on disinfection container 806, which can contain a disinfection solution such as citric acid. The disinfection configuration places the paddles 813 and 814 on the opposite side of the caddy 801 as in the dialysis configuration shown in FIG. 13*a*. The same pumps and valves as described for movement of sodium chloride, sodium bicarbonate or cation infusates can be used to direct fluid from the citric acid container 806 into the dialysis system. The citric acid container 806 can allow circulation between multiple connectors during cleaning or disinfection. For example, fluid can pass between connectors 811 and 810 through citric acid container 806 to allow cleaning or disinfection fluid to be circulated through connectors 815 and 816 by action of a single pump. The infusate caddy 801 can be constructed so that one or more connectors are blocked, and therefore sealed when the caddy 801 is placed in the disinfection configuration. Only the connectors necessary to move citric acid from the citric acid container 806 to the dialysis system can be open to allow fluid movement.

Alternatively, a second caddy can be used for disinfection. A second caddy, containing a disinfection container, can fit into the dialysis machine in the same receiving slot as the first caddy. The second caddy can include one or more fitting features to ensure that connectors on the disinfection container will align with the paddles or other caddy connectors when the second caddy is inserted into the receiving slot. However, a second caddy is not necessary, and a disinfection container can be directly connected to the caddy connectors for disinfection.

FIG. 13*c* shows a top view of a caddy 801 in a dialysis configuration. As is shown in FIG. 13*c*, sodium chloride container 805 is connected to paddle 824, cation infusate container 803 is connected to paddle 814 and sodium bicarbonate container 804 is connected to paddle 813. Disinfection container 806 is not connected to any paddles in FIG. 13*c*. As shown in FIG. 13*c*, disinfection container 806 includes three connectors 810, 811, and 823. When the caddy 801 is placed in the disinfection configuration, all of the paddles will be connected to disinfection container 806. Paddle 813 can connect to connector 823, paddle 814 can connect to connector 811, and paddle 824 can connect to connector 810. Curved wedge protrusion 828 is a fitting feature to ensure proper placement of sodium bicarbonate container 804 and cation infusate container 803. Curved wedge protrusion 829 is a fitting feature to ensure proper placement of sodium chloride container 805 and citric acid container 806. Similarly, curved corner protrusions 830 at each corner of the receiving compartment 802 can ensure the proper seating of the caddy 801.

Figure 13D:
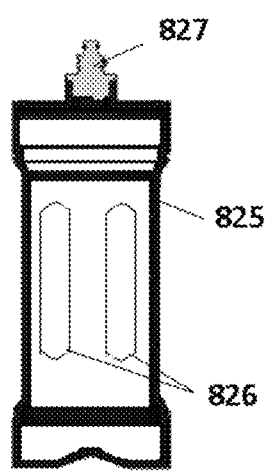
FIG. 13d shows a container with ridges on the exterior of the container to ensure complementary fitting in a caddy.

FIG. 13*d* shows an example of a container wherein the fitting features designed to keep the container in place are a series of ridges. Container 825 can be constructed with one or more ridges 826. The interior of the caddy corresponding to the unique location for container 825 can have a series of complementary corresponding grooves. The container 825 can only be placed in the caddy in the unique position where the complementary grooves in the interior of the caddy align with the ridges 826 on the exterior of the container 825. Other containers can have differently sized ridges, differently spaced ridges, and/or a different number of ridges. The caddy can be constructed with the proper corresponding grooves for each container in the correct location. Because the containers can only be positioned in the caddy where the corresponding ridges and grooves are complementary, these features can ensure the proper position for each container. When the caddy is connected to the dialysis machine, connector 827 on container 825 will align with the proper paddle or other connector on the system to ensure that the proper solution is added to the dialysis system in the proper amounts and at the proper location. One skilled in the art will understand that the grooves can be constructed on the containers and the ridges on the caddy.

Figure 14A:
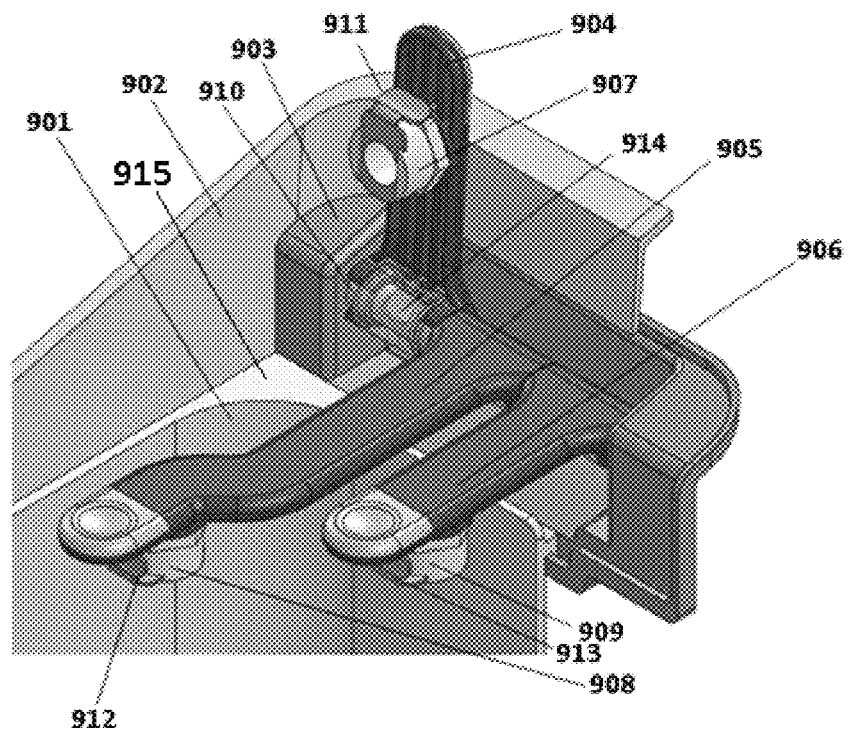
FIG. 14a shows a close-up view of a paddle assembly with an infusate caddy and dialysis machine.
Figure 14B:
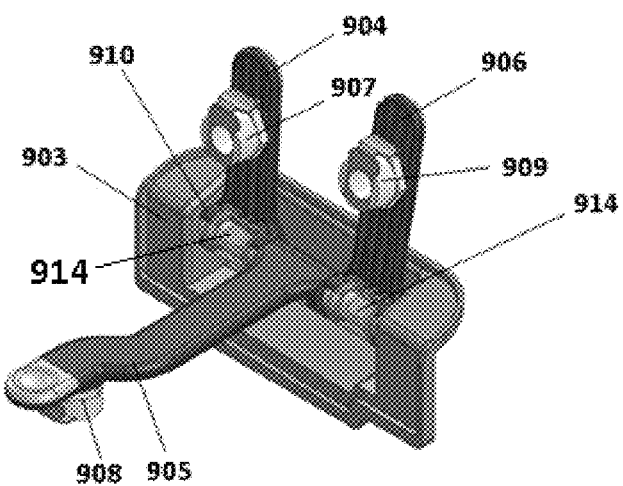
FIG. 14b shows a close-up view of a paddle assembly removed from a dialysis machine.
Figure 14C:
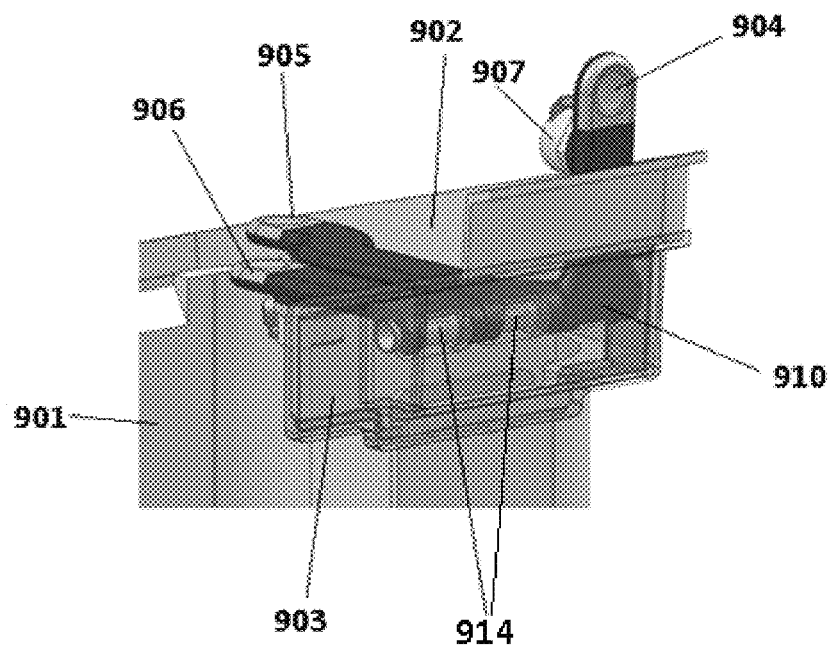
FIG. 14c shows a reverse view of a paddle assembly on a dialysis machine.

FIGS. 14*a*, 14*b*, and 14*c* show a close up view of the paddle assembly described. FIG. 14*a* shows the paddle assembly 903 with an empty caddy 901 on receiving compartment 902. One paddle 904 is in the up, or disconnected position. The other two paddles 905 and 906 are in the down position, or the position the paddles will be in when attached to the containers. FIG. 14*b* shows a floating paddle assembly 903 with paddles 904 and 906 in a disconnected position and paddle 905 in a connected position. Such configuration can be used for specific needs for a flow path only requiring connection between fluid connector 912 and a properly connected infusate container. Each paddle can be moved between positions on a hinge, such as hinge 910. FIG. 14*c* shows a rear view of the paddle assembly 903 showing a hinge 910 as viewed from a back side of dialysis machine and viewing the an empty receiving compartment 902. Each of the paddles can be moved independently of the other paddles, as shown in FIGS. 14*a* and 14*b*. The single hinge 910 of FIG. 14*c* can be used and all paddles can be moved together. As shown in FIG. 14*a*, each paddle 904, 905, and 906 can have a paddle connector 907, 908, and 909 for connection to a container as described. Locking mechanism components 911, 912, and 913 can lock the paddles to the container connectors as described. The locking mechanisms on each paddle can be adapted to a particular container. The paddle assembly can also include a mechanism to hold one or more paddles in the disconnected position. For example, the paddles or hinge can include a locking mechanism (not shown) that locks the paddles in either the open or closed position until a user unlocks the mechanism to allow the paddles to move. The paddles can connect tightly to the hinge. The friction caused by the connection between the paddles and the hinge can cause the paddles to remain in either the connected or unconnected position until an external force is applied to the paddles, such as by a user. Further, the curved corner protrusion 915 can ensure proper seating of an infusate caddy and hence, proper alignment of the paddle connectors 907, 908, and 909.

Any of the fluid lines can be placed within the paddles for easy connection of the containers to the dialysis system. Paddle 904 may connect to the cation infusate container as described. The paddle connector 907 positioned on the distal end of paddle 904 may be in fluid communication with the corresponding connector on the cation infusate container. The hinge 910 can be a hollow hinge having a central flow line in communication with fluid lines in the paddles. A fluid line may run from the paddle connector 907, through the paddle 904, and through the hollow portion 914, defining a central flow line of hollow hinge 910. The fluid line can further connect into the appropriate position of the dialysate flow loop. By using the paddles themselves as the fluid lines, connection of each container to the proper position in the dialysate flow loop can be assured. Curved corner protrusion 915 at each corner of the receiving compartment 902 can ensure the proper seating of the caddy 901.

Figure 15A:
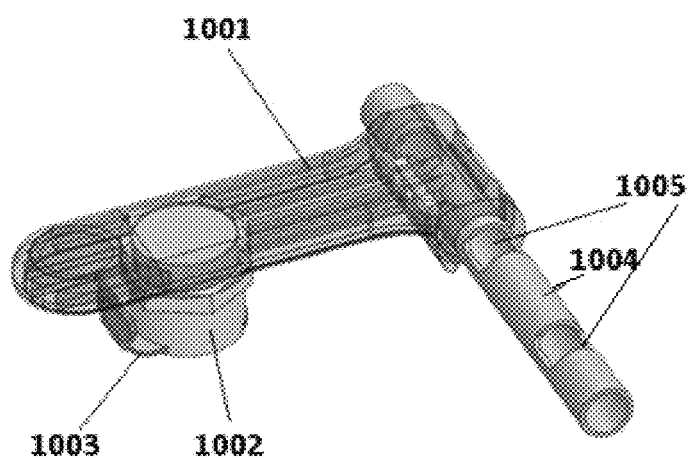
FIG. 15a shows a detailed view of a paddle attached to a hinge.
Figure 15B:
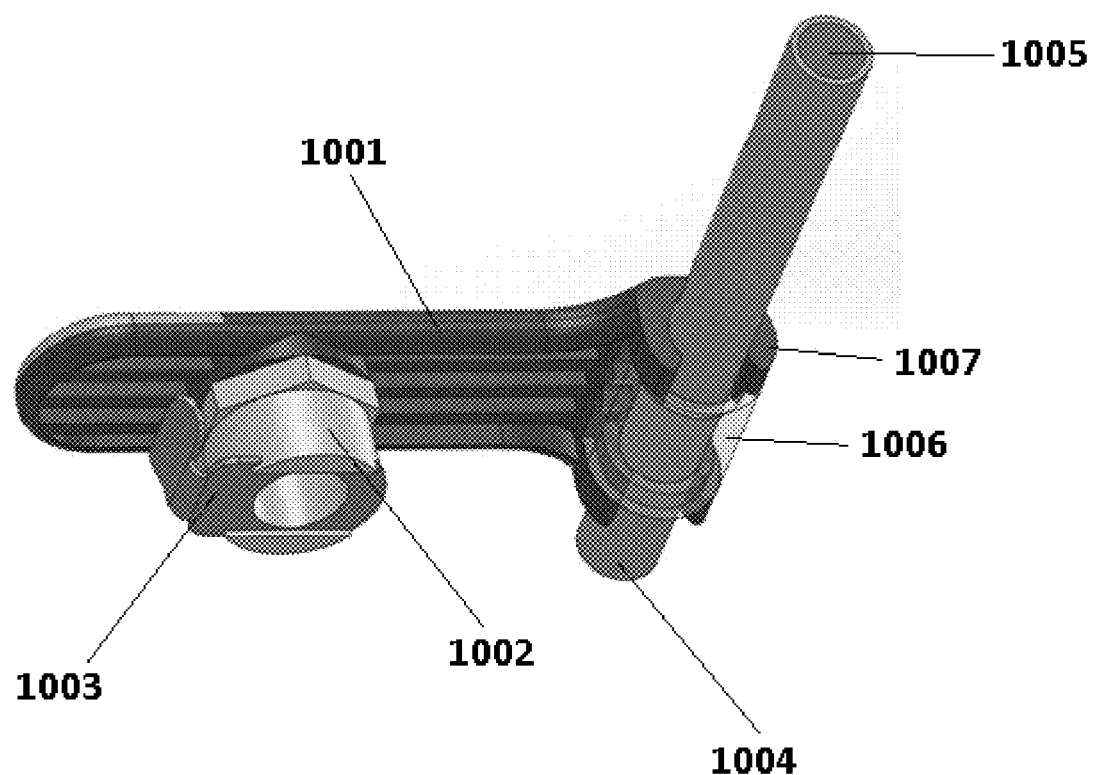
FIG. 15b shows a bottom view of a paddle attached to a hinge.
Figure 15C:
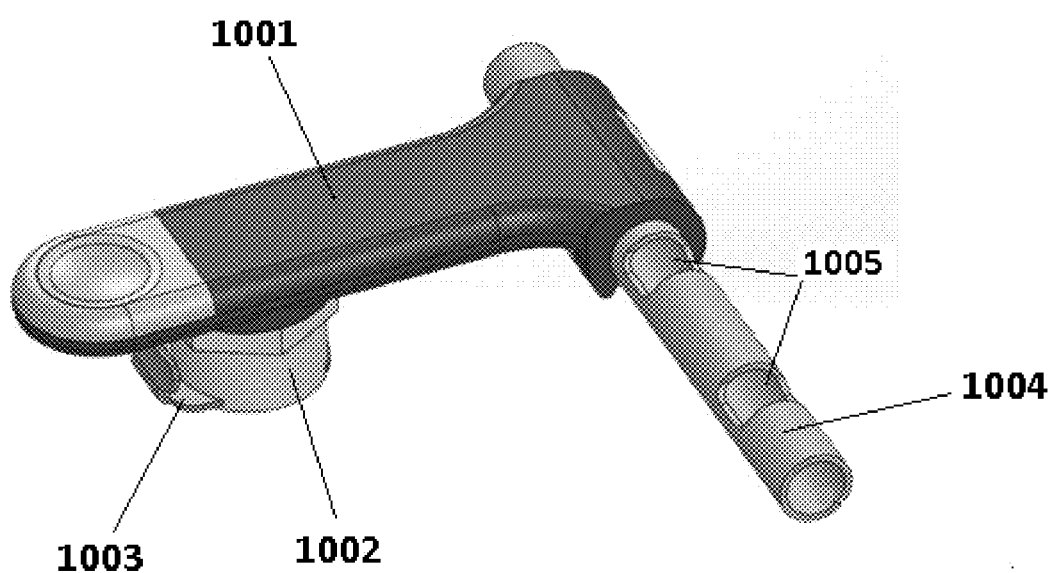
FIG. 15c shows a top view of a paddle attached to a hinge.
Figure 15D:
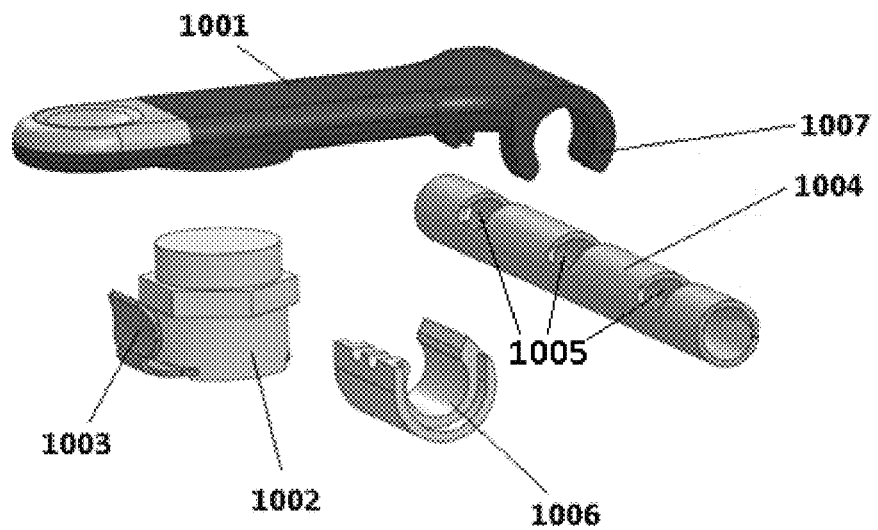
FIG. 15d shows an exploded view of a paddle.

FIGS. 15a, 15b, 15c and 15d show detailed views of one paddle of the paddle assembly and the hinge used for moving the paddles. The paddles 906 and 905 from FIG. 14c are not shown in FIGS. 15a-d for illustrative reasons. The paddle 1001 can be connected to hinge 1004 through any means known in the art. The connection of the paddle 1001 to the hinge 1004 allows the paddle 1001 to rotate up and down with respect to the hinge 1004. When placed in the down position, the paddle 1001 can connect to a container containing fluid for use during or after dialysis, wherein the infusate container can connect to paddle connector 1002. Locking mechanism 1003 can lock the paddle connector 1002 to the corresponding container connector. The paddle 1001 can be locked into position on hinge 1004, so the paddle 1001 cannot move independently of the hinge 1004. The entire hinge 1004 can be constructed so the hinge 1004 can itself rotate, allowing the paddle to move between an up and a down position. The paddle 1001 can be connected to hinge 1004 such that the paddle 1001 can be rotated independently of hinge 1004. The hinge 1004 can be constructed such that the hinge 1004 cannot rotate, but so that the paddle 1001 can rotate around the hinge. Such a configuration allows each of the paddles to be independently moveable of the other paddles. In a top view FIG. 15b, access points 1005 on the hinge 1004 provide fluid access to the two invisible paddles. The fluid line can run from paddle connector 1002, through the paddle 1001 and into the access portions 1005 of hinge 1004. The hinge 1004 can be hollow, allowing for the fluid line to pass through the access points 1005 and into the two invisible paddles. If attached to a container, fluid can travel from the container, through the paddle 1001 and into a dialysis machine. FIG. 15d shows an exploded paddle 1001. The paddle 1001 can include paddle attachment portion 1007. The paddle attachment portion 1007 can fit around hinge 1004. Hinge attachment 1006 can fit on the opposite side of the hinge 1004 as the paddle attachment portion 1007 as shown in underside view of FIG. 15b. If both the paddle attachment portion 1007 and the hinge attachment 1006 are placed onto the hinge 1004, engagement members on the hinge attachment 1006 can connect to corresponding engagement members on the paddle attachment portion 1007, as shown in FIG. 15b, on the paddle 1001. The engagement members on each of the hinge attachment 1006 and paddle attachment portion 1007 can provide a locking action to allow the paddle 1001 to rotate around the hinge 1004, but also preventing the paddle 1001 from inadvertent removal from the hinge 1004.

As described herein, the caddy and containers can be sized and shaped to ensure that the containers are placed within the caddy in the correct locations, ensuring that each of the containers is connected to the proper connectors, pumps and valves to carry out both dialysis and disinfection. FIG. 16 shows several views describing the canister registration, ensuring that all containers are connected to the correct connectors.

Figure 16A:
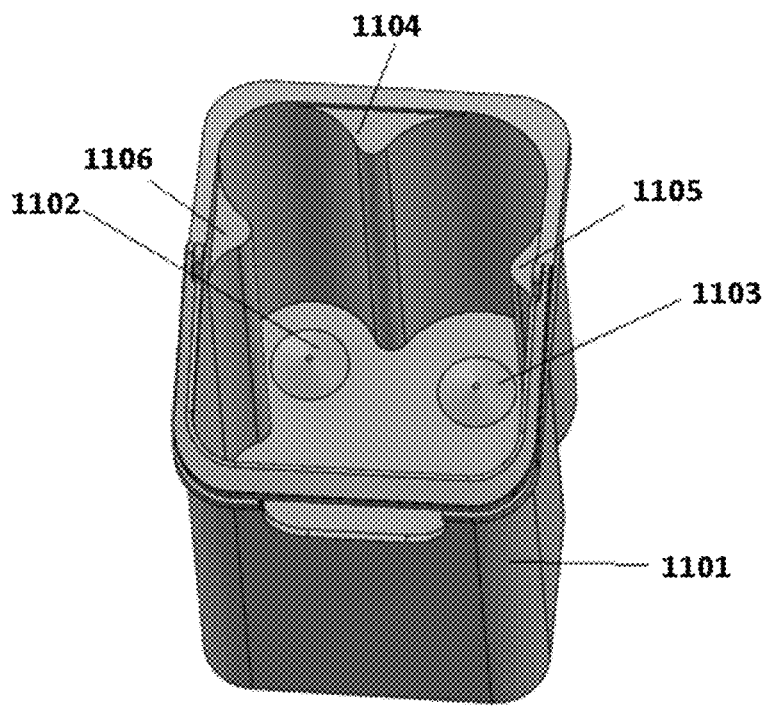
FIG. 16a shows an empty infusate caddy for container registration.

FIG. 16a shows an empty caddy 1101. As described herein, the caddy can include receiving compartments, which are specific and unique positions for each of the containers. Position 1103 is a receiving compartment shown for a sodium chloride container, position 1102 is a receiving compartment shown for a sodium bicarbonate container, and a third receiving compartment (not shown) can be available for a cation infusate container. The caddy can have fitting features to ensure that only the correct containers can fit within each receiving compartment. Fitting features 1104, 1105, and 1106 can accomplish the function. Fitting features 1104 and 1106 define the geometry, shape and size of the container that can fit in position 1102. Fitting features 1104 and 1105 define the geometry, shape and size of the container that can fit in position 1103. As position 1102 is not the same size position 1103, the sodium bicarbonate container will not fit in position 1103 and the sodium chloride container will not fit in position 1102.

Figure 16B:
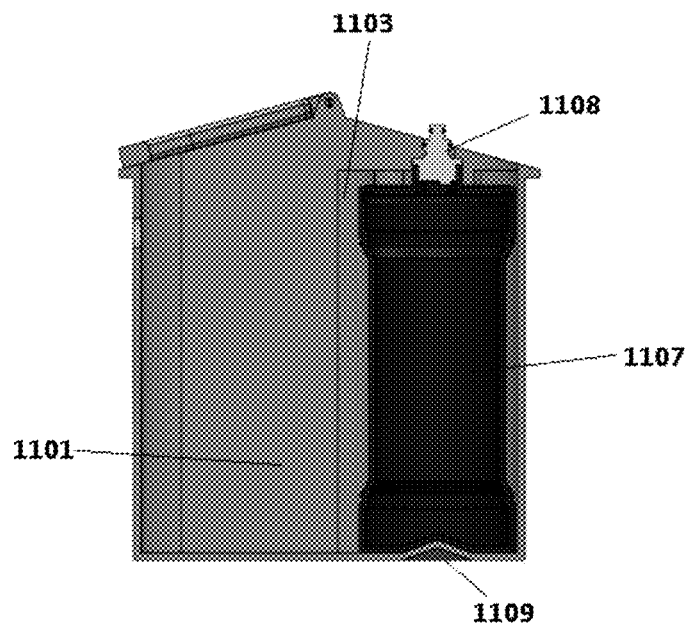
FIG. 16b shows an infusate caddy with a sodium bicarbonate container.

FIG. 16b shows a sodium bicarbonate container 1107 in place in position 1103. Because of the size and shape of the fitting features included in the caddy and containers, sodium bicarbonate container 1107 is the only container that can fit into position 1103. Once in place, a connector, such as the paddles described, can be connected to bicarbonate connector 1108 to allow the sodium bicarbonate to be used in dialysis. The base of the caddy 1101 can include a fitting feature 1109 that corresponds to a complementary fitting feature on the base of the sodium bicarbonate container 1107, further serving to ensure that only sodium bicarbonate container 1107 can fit into position 1103 and to ensure that the sodium bicarbonate container 1107 is properly secured within the position 1103.

Figure 16C:
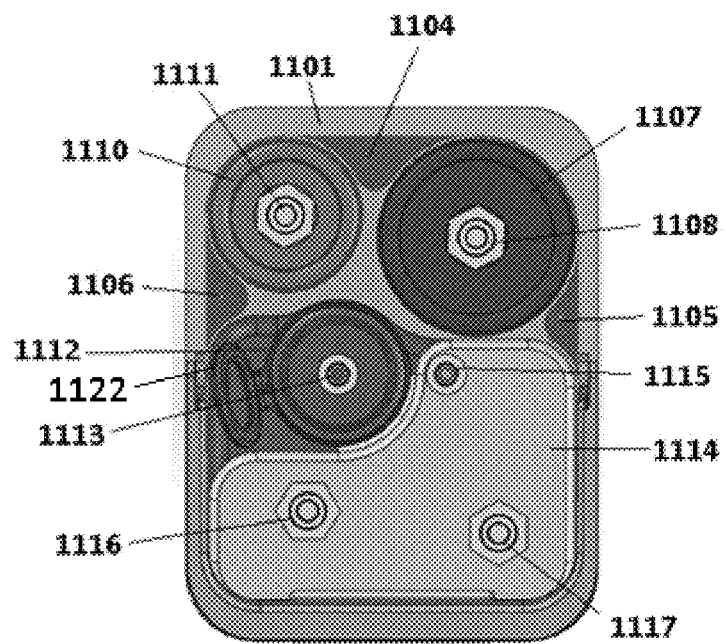
FIG. 16c shows a top view of an infusate caddy after all containers have been added to the infusate caddy.

FIG. 16c shows an infusate caddy 1101 after each of the containers has been placed within the infusate caddy 1101. Sodium bicarbonate container 1107 can fit into a position defined by fitting features 1104 and 1105. Sodium chloride container 1110 can fit into a position defined by fitting features 1104 and 1106. Cation infusate container 1112 can fit into a position defined by fitting features 1105 and 1106. As such, each of the containers can only fit into the proper position within the caddy, ensuring that sodium chloride connector 1111, sodium bicarbonate connector 1108 and cation infusate connector 1113 can only connect to the proper connectors, pumps and valves of the dialysis machine. The caddy 1101 can include a disinfection container 1114. If the caddy 1101 is placed in a disinfection configuration, disinfection connectors 1115, 1116 and 1117 can connect to the proper connectors, pumps and valves in the dialysis machine to carry out disinfection.

Figure 16D:
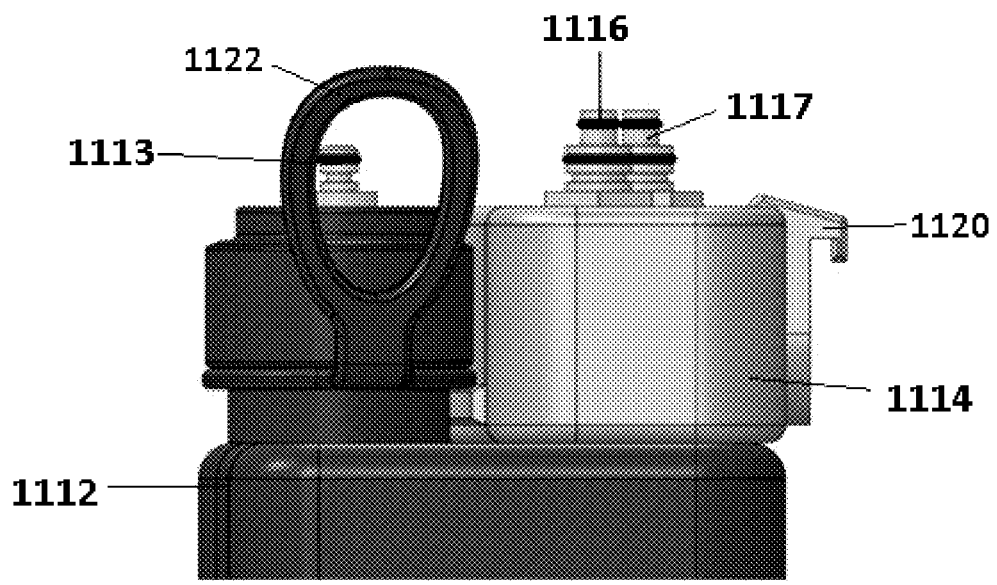
FIG. 16d shows a close up view of a disinfection container and cation infusate container fitted together.
Figure 16E:
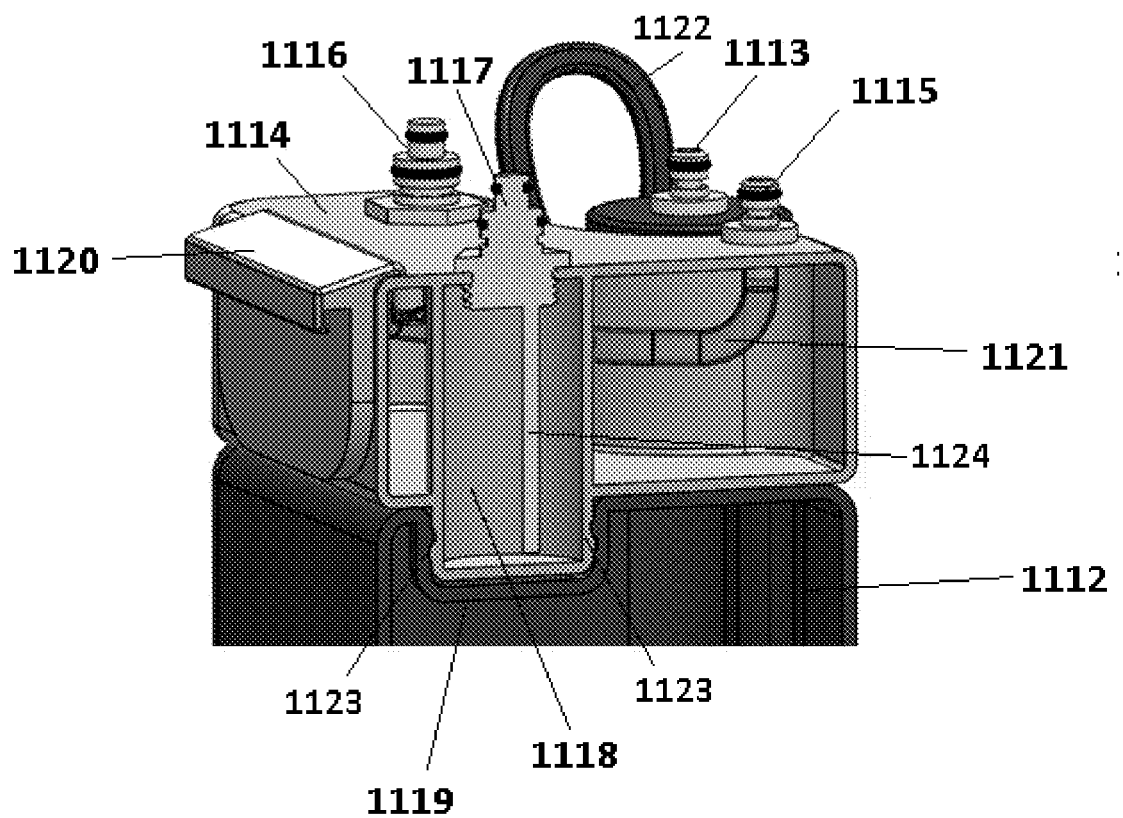
FIG. 16e shows a cut-away view of a disinfection container and cation infusate container fitted together.

FIG. 16d shows a left side view of the disinfection container 1114 in an infusate caddy, while FIG. 16e shows a right side cutaway view. In order to save space, the disinfection container 1114 and cation infusate container 1112 can include fitting features, such as by being sized and shaped so that the disinfection container 1114 fits on top of cation infusate container 1112. One skilled in the art will understand that any containers can be sized and shaped to fit on top of one another, and is not limited to the disinfection container 1114 and cation infusate container 1112.

In order to ensure that the disinfection container 1114 is properly configured in the infusate caddy 1101 for disinfection, the disinfection container 1114 and cation infusate container 1112 can each have fitting features to ensure proper insertion and alignment of the disinfection container 1114. Non-limiting examples of such fitting features are illustrated in FIG. 16e. Disinfection container 1114 can include separate container 1118, which can hold a solid disinfectant source or any other substance. Container 1118, which is integral to disinfectant container 1114, can fit into indentation 1119 built into cation infusate container 1112. Because container 1118 can only fit into indentation 1119 in a single configuration, in order for disinfection container 1114 to fit on top of cation infusate container 1112, the disinfection container 1114 must be in the proper configuration for use in disinfection. Ridges and indentations 1123 on container 1118 and cation infusate container 1112 are complementary fitting features that securely lock container 1118 into place on cation infusate container 1112. Fluid line 1124 in container 1118 provides for access to fluid in a bottom section of container 1118. Disinfection container 1114 can also or alternatively include fitting feature flap 1120. Flap 1120 can fit over the edge of the infusate caddy (not shown in FIG. 16e), ensuring that the disinfection container 1114 is in the proper location inside of the infusate caddy. During disinfection, disinfection fluid, such as citric acid, can flow through line 1121 and into the dialysis system. Any one or more of the infusate containers can include a handle, such as handle 1122 on cation infusate container 1112.

Each of the connectors can have a size and shape keyed to a particular fluid connector on the dialysis machine. In FIGS. 16a-e, connectors 1113 and 1115 are rounded, while connectors 1108, 1111, 1116, and 1117 are hexagonal. Each of the corresponding fluid connectors disposed on the dialysis machine can have a size and shape to only engage with the connectors on the proper infusate containers. As illustrated in FIGS. 16a-e, each of fluid connectors on the infusate containers can include an o-ring or other sealing mechanism to prevent leakage when connected.

Figure 17:
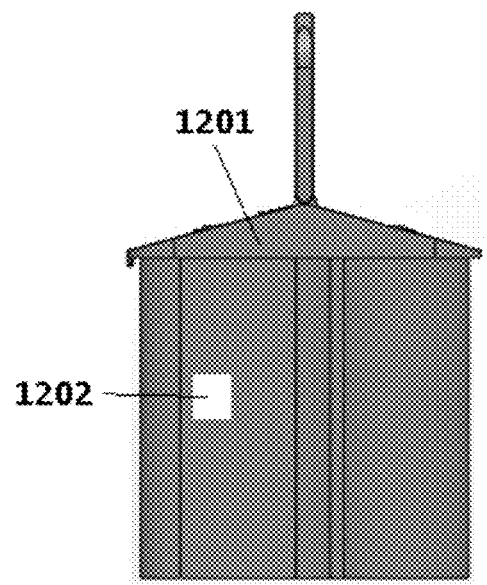
FIG. 17 shows a caddy including a sensor for sensing a configuration of the caddy.

The infusate caddy can include a sensor, as shown in FIG. 17, as a mechanism to detect whether the caddy is in a dialysis configuration or a disinfection configuration. Caddy 1201 can include sensor 1202 affixed to the caddy. Although in FIG. 17, the sensor is shown on the side of the caddy, one skilled in the art will understand that the sensor can be placed anywhere on the caddy, including the base of the caddy or the inside portion of the caddy. Sensor 1202 can interact with a corresponding sensor, detector, or other component on the dialysis machine (not shown). When the caddy is placed into the dialysis machine, the position of the sensor 1202 can be detected, thus determining the orientation of the caddy. The dialysis machine can be configured to become disabled if the caddy is in an incorrect configuration. For example, the dialysis machine can shut down if a user attempts to begin a dialysis session while the caddy is in the disinfection orientation. Similarly, the dialysis machine can shut down if the user attempts to disinfect the system while the caddy is in the dialysis configuration.

Sensor 1202 can be any type of sensor known in the art for determining the configuration of the caddy, including a Hall sensor. A Hall sensor is a component that varies a voltage output based on distance from a magnetic field. As such, either the dialysis machine or the sensor component 1202 can emit a magnetic field. The Hall sensor, located on the other component from the magnetic field emitter can thus determine the distance from the magnetic field emitter. The distance from the magnetic field emitter can inform the system and user which of the caddy configuration. Alternatively, the sensor 1202 can be a magnetic sensor. A corresponding magnet can be placed on the dialysis machine. When the caddy is placed in the dialysis machine, the magnetic sensor can determine whether the magnet is aligned with the sensor, and thus the orientation of the caddy.

The caddy can additionally or alternatively include a tracking component, such as a barcode or radio frequency identification component (RFID). The tracking component allows for the system to match the infusates or other components in the caddy with a particular patient and machine. Before use, the user can be prompted to scan the barcode or RFID. The system can ensure that the proper caddy is matched up to the proper patient, thus ensuring that the patient receives the correct infusates based on the patient's dialysis prescription. The dialysis machine can also include a tracking component. Before use, the system can ensure that the caddy matches up to a correct dialysis machine, ensuring that the proper patient is using the proper dialysis machine with the proper caddy containing the proper sets of containers. The tracking component can be a writable RFID. The system can write a patient specific identifier onto the tracking component. When the infusate caddy is filled with containers, the RFID on the caddy can be checked against the patient prescription to ensure that the proper containers are filled and placed within the caddy for a specific patient. When the caddy is filled with the solute containers, the prescription itself be written onto the RFID. When the caddy is inserted into the dialysis machine, the system can read the prescription and ensure that the prescription matches with the correct patient.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A fluid flow path, comprising:
one or more conduits fluidly connectable to a dialyzer;
at least one fluid line on the fluid flow path, said at least one fluid line fluidly connectable to at least one detachable container;
a fluid pump positioned on the at least one fluid line for removing or introducing a fluid to the at least one detachable container of at least two detachable containers;
a fluid connector fluidly connectable to the at least two detachable containers wherein the at least two detachable containers are selected from the group consisting of a sodium chloride infusate container, a sodium bicarbonate infusate container, and a cation infusate container;
wherein each detachable container has at least one fitting feature complementary to an infusate caddy; wherein the infusate caddy has at least one fitting feature disposed on an interior surface of the infusate caddy; the at least one fitting feature defining at least two receiving compartments in the infusate caddy; wherein every receiving compartment included in the infusate caddy has a size and/or shape different from every other receiving compartment included in the infusate caddy; each of the at least two receiving compartments in the infusate caddy complementary to one of the at least two detachable infusate containers; wherein at least one fitting feature on each detachable container is complementary and of a unique size to the at least one fitting feature on the interior surface of the infusate caddy;
wherein the at least one fitting feature disposed on the interior surface of the infusate caddy is configured to define only one arrangement of the at least two detachable containers within the infusate caddy.

2. The fluid flow path of claim 1, further comprising a paddle assembly having at least one independently movable paddle, wherein the fluid connector is positioned at a distal end of the at least one paddle; wherein the fluid connector fluidly connects the at least two detachable containers to the at least one fluid line on the fluid flow path.

3. The fluid flow path of claim 1, wherein the at least one fluid line comprises at least a first fluid line fluidly connectable to the sodium chloride infusate container; and a second fluid line fluidly connectable to the sodium bicarbonate infusate container; wherein the first fluid line and the second fluid line are in fluid connection with the fluid flow path.

4. The fluid flow path of claim 3, wherein the at least one fluid line comprises a third fluid line; wherein the first fluid line and second fluid line connect to a first valve wherein the first valve connects to the third fluid line; wherein the third fluid line connects to the fluid flow path; and wherein the fluid pump controls movement of fluid between the fluid flow path and the sodium chloride infusate container and the sodium bicarbonate infusate container.

5. The fluid flow path of claim 4, wherein the at least one fluid line comprises at least a fourth fluid line and a fifth fluid line; wherein the fourth fluid line is fluidly connectable to the sodium chloride infusate container and the fifth fluid line is fluidly connectable to the sodium bicarbonate infusate container; wherein the fourth fluid line and the fifth fluid line are fluidly connected to a second valve; wherein the second valve connects the fourth fluid line and fifth fluid line to a sixth fluid line; and wherein the sixth fluid line connects the second valve to the fluid flow path.

6. The fluid flow path of claim 5, wherein the at least one fluid line comprises at least a seventh fluid line; wherein the fourth fluid line and the fifth fluid line are connected into the seventh fluid line; wherein the seventh fluid line connects to the second valve;
wherein the second valve connects the seventh fluid line and the sixth fluid line; and wherein the sixth fluid line connects the second valve to the fluid flow path.

7. The fluid flow path of claim 6, wherein the second valve is either a two way valve or a three way valve.

8. The fluid flow path of claim 1, wherein the fluid pump is a bi-directional pump.

9. The fluid flow path of claim 1, wherein the at least one fluid line comprises at least one fluid line fluidly connectable to a disinfectant container in the infusate caddy.

10. The fluid flow path of claim 5, wherein the at least one fluid line comprises at least a seventh fluid line and an eighth fluid line; wherein the third fluid line is connected to a third valve;
wherein the third valve connects to the seventh fluid line and the eighth fluid line; wherein the seventh fluid line connects to the fluid flow path downstream of a sorbent cartridge and the eighth fluid line connects to the fluid flow path upstream of the sorbent cartridge.

11. A method, comprising the steps of:
selectively opening or closing one or more valves in the fluid flow path of claim 1;
pumping the fluid using the fluid pump from the at least one detachable container through the fluid connector into a dialysate flow path through the at least one fluid line;
wherein the at least one detachable container is seated within the infusate caddy and contains at least one solute for use in dialysis.

12. The method of claim 11, wherein the infusate caddy is seated inside a receiving compartment of a dialysis machine.

13. The method of claim 11, further comprising the step of pumping the fluid from the dialysate flow path into the at least one detachable container through the fluid connector.

* * * * *